(12) United States Patent
Ho et al.

(10) Patent No.: US 11,492,635 B2
(45) Date of Patent: Nov. 8, 2022

(54) METHOD FOR IMPROVING STRESS TOLERANCE OF PLANTS

(71) Applicant: Academia Sinica, Taipei (TW)

(72) Inventors: Tuan-Hua Ho, Taipei (TW); I-Chieh Tseng, Taipei (TW); Su-May Yu, Taipei (TW); Shuen-Fang Lo, Taipei (TW)

(73) Assignee: ACADEMIA SINICA, Taipei (TW)

( * ) Notice: Subject to any disclaimer, the term of this patent is extended or adjusted under 35 U.S.C. 154(b) by 32 days.

(21) Appl. No.: 15/923,288

(22) Filed: Mar. 16, 2018

(65) Prior Publication Data

US 2018/0320192 A1 Nov. 8, 2018

Related U.S. Application Data

(60) Provisional application No. 62/472,669, filed on Mar. 17, 2017.

(51) Int. Cl.
*C12N 15/82* (2006.01)
*C07K 14/415* (2006.01)

(52) U.S. Cl.
CPC ........ *C12N 15/8271* (2013.01); *C07K 14/415* (2013.01); *C12N 15/8273* (2013.01)

(58) Field of Classification Search
None
See application file for complete search history.

(56) References Cited

U.S. PATENT DOCUMENTS

| 10,266,838 B2* | 4/2019 | Yu | C12N 15/8293 |
| 2004/0123343 A1* | 6/2004 | La Rosa | C07K 14/415 |
| | | | 800/278 |
| 2006/0218662 A1* | 9/2006 | Hammer | C12N 15/8216 |
| | | | 800/278 |

OTHER PUBLICATIONS

Tseng et al. (Plant Physiology 163.1 (2013): 118-134). (Year: 2013).*
Datta et al. (Plant biotechnology journal 10.5 (2012): 579-586). (Year: 2012).*

* cited by examiner

*Primary Examiner* — Charles Logsdon
(74) *Attorney, Agent, or Firm* — Birch, Stewart, Kolasch & Birch, LLP

(57) ABSTRACT

The present invention relates to a method of improving stress tolerance and/or preventing growth reduction of a plant by introducing a polynucleotide encoding a Repetitive Proline-rich Protein (RePRP) into the plant.

16 Claims, 7 Drawing Sheets

Specification includes a Sequence Listing.

METHOD FOR IMPROVING STRESS TOLERANCE OF PLANTS

RELATED APPLICATIONS

This application claims the benefit of U.S. provisional application No. 62/472,669, filed Mar. 17, 2017 under 35 U.S.C. § 119, the entire content of which is incorporated herein by reference.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2018-06-12_5992-0208PUS1_ST25.txt" created on Jun. 12, 2018 and is 29,245 bytes in size. The sequence listing contained in this .txt file is part of the specification and is hereby incorporated by reference herein in its entirety.

TECHNOLOGY FIELD

The present invention relates to use of a Repetitive Proline-rich Protein (RePRP) for modifying features of transgenic plants overly expressing it.

BACKGROUND

Environmental abiotic stresses such as drought, extreme temperatures, and flooding have caused significant crop losses in agricultural output as global climate change has worsened in recent years. It has been estimated that as much as two thirds of the yield of major crops are routinely lost due to adverse/stressful environments (see Boyer, 1982). Intense study is under way to understand how plants survive and how to minimize the impact of abiotic stresses on crop yield.

Most of the tolerance mechanisms associated with water-deficit stresses are related to osmotic adjustments, maintenance of ionic homeostasis, and removal of damaging reactive oxygen species (see Kar, 2011). The basic architectural features of plants are also known to be adjusted under stress, such as increased waxes on the surface, sunken stomata, and facilitation of leaf rolling.

Abscisic acid (ABA) is the most commonly recognized stress hormone during water-deficit stress. ABA can (i) cause stomata in leaves to close in order to reduce transpiration, and (ii) enhance the expression of other genes needed for the establishment of stress tolerance.

Rice plant growth and development readjusts to avoid unnecessary growth in the shoot, thereby reducing water loss under the stress of severe water deficit or upon treatment with high concentrations of ABA. Rice roots become shorter, thicker, and heavier, resulting from the accumulation of biomass synthesized from surplus nutrients transported from the shoots.

A group of highly proline rich glycoproteins ("Os-RePRPs") is highly induced in rice roots by ABA, salinity, and drought (see Tseng et al., 2013). OsRePRPs, which are localized to the plasma membrane where they interact with cell wall polysaccharides, are necessary and sufficient for making roots shorter and thicker. No reports demonstrate their effects in stress tolerance and growth of plants.

Some approaches have been developed to improve plant stress tolerance. However, plants survival under stress often exhibit growth retardation which is negative to productivity and cannot satisfy the need in agriculture. The need still exists to provide an approach to breed plants with tolerance to multiple stresses that still maintain growth and productivity.

SUMMARY

The present disclosure is based, at least in part, on the unexpected findings that expression of a Repetitive Proline-rich Protein (RePRP) results in improved stress tolerance, especially causes no substantial effects in growth retardation in transgenic plants overly expressing such. Compared with a control (wild type) plant without transformation with a RePRP gene, the transgenic plants of the invention exhibit significant increase in survival rate without substantial reduction of growth under stress conditions. The transgenic plants of the invention also exhibits a less level of yield reduction under stress conditions compared with a control (wild type) plant.

Therefore, the present invention provides a method of improving stress tolerance and/or preventing growth reduction of a plant, comprising:

(a) transforming plant cells with a vector comprising a nucleic acid operably linked to a promoter to obtain recombinant plant cells expressing a RePRP protein, wherein the nucleic acid encodes the RePRP protein;

(b) growing the recombinant plant cells obtained in (a) to generate a plurality of transgenic plants; and (c) selecting a transgenic plant from the plurality of transgenic plants generated in (b) that exhibits an improved tolerance to stress or substantially no growth reduction or a combination thereof, as compared with a non-transgenic plant counterpart growing under the same conditions.

In some embodiments, the transgenic plant exhibits less yield reduction as compared with the non-transgenic plant counterpart.

In some embodiments, the RePRP protein comprises the amino acid sequence of SEQ ID NO: 1, 2, 3 or 4.

In some embodiments, the promoter is heterologous to a naturally occurring gene encoding the RePRP protein.

In some embodiments, the promoter is a constitutive promoter or an inducible promoter.

In some embodiments, the promoter is a constitutive promoter selected from the group consisting of a maize ubiquitin (Ubi) promoter, a rice actin (Act1) promoter, and a cauliflower mosaic virus 35S (CaMV35S) promoter.

In some embodiments, the promoter is an inducible promoter selected from the group consisting of an *Arabidopsis* cor1 SA promoter, an *Arabidopsis* kin1 promoter, an *Arabidopsis* heat-shock factor (HSF) promoter, an *Arabidopsis* kin1 promoter, an *Arabidopsis* rd29A promoter, an alpha-amylase promoter and a synthetic ABRC321 promoter.

In some embodiments, the promoter is 3XABRC321.

In some embodiments, the transgenic plant is a monocot plant. Examples of a monocot plant include rice, barley, wheat, rye, oat, corn, bamboo, sugarcane, onion, leek and ginger.

In some embodiments, the transgenic plant is a dicot plant. Examples of a dicot plant include *Arabidopsis*, soybean, peanut, sunflower, safflower, cotton, tobacco, tomato, pea, chickpea, pigeon pea or potato.

In some embodiments, the stress is biotic stress or abiotic stress.

In some embodiments, the stress is abiotic stress including osmotic stress, drought stress, salt stress, or a combination thereof.

The details of one or more embodiments of the invention are set forth in the description, in the drawings, and in the examples below. Other features, objects, and advantages of the invention will be apparent from the detailed description of several embodiments and also from the claims. All publications and patent documents cited herein are incorporated by reference in their entirety.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 5A shows that the survival rate of ABRC321:OsRePRP2.1 transgenic plants (T2 generation) was significantly higher than that of TNG67. Data are means ±SD from two experimental repeats. FIG. 5B shows similar root image of 14-day old rice seedlings of wild type and ABRC321:OsRePRP2.1 plants.

FIG. 6A shows 50-day-old matured *Arabidopsis* plants grown under normal conditions. FIG. 6B shows root image of 10-day-old *Arabidopsis* seedlings grown on the normal agar plate. FIG. 6C shows the root length data expressed by the means ±SD from each lines.

DETAILED DESCRIPTION

Figure 1:
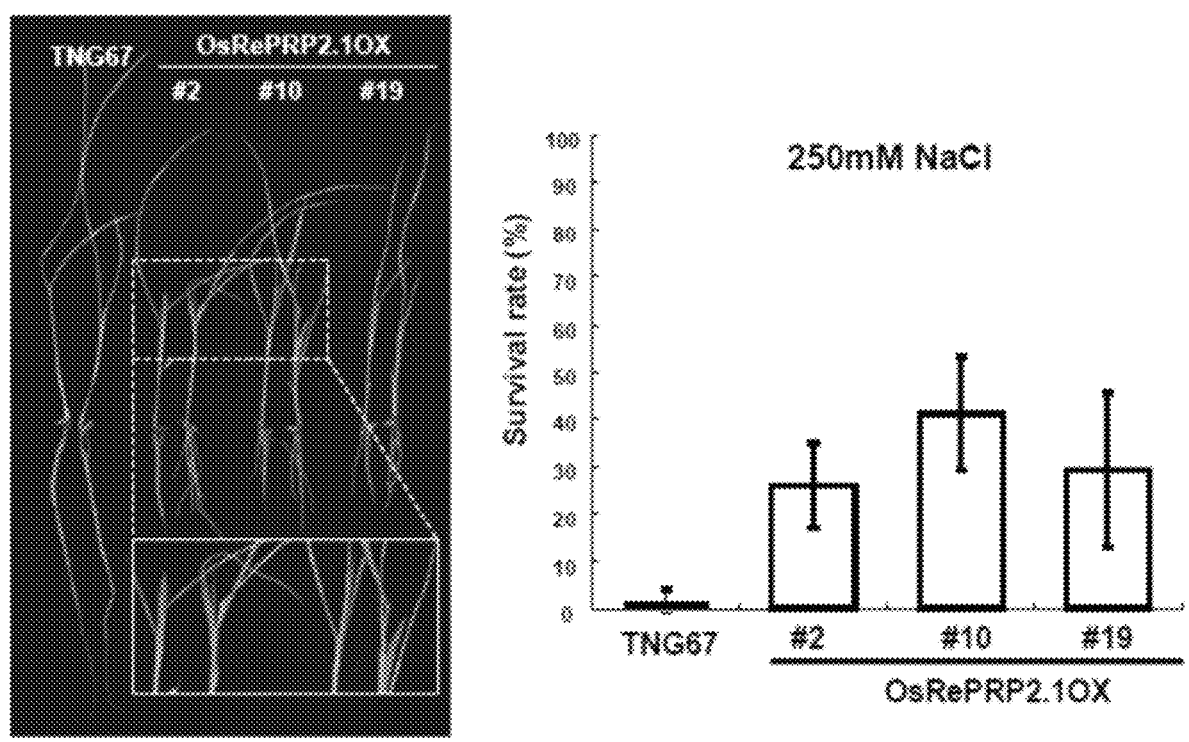
FIG. 1 shows that OsRePRP2.1 over-expression enhanced salinity tolerance in rice. Three-leaf old seedlings were treated with 250 mM NaCl for 5 days, and then recovered to normal condition for 12 days. The survival rate of OsRePRP2.1OX transgenic plants was significantly higher than TNG67. Data are means ±SD from three experimental repeats.

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "comprise" or "comprising" is generally used in the sense of include/including which means permitting the presence of one or more features, ingredients or components. The term "comprise" or "comprising" encompasses the term "consists" or "consisting of."

The present studies found that, unexpectedly, Repetitive Proline-rich Proteins (RePRPs) improved features of transgenic plants overly expressing such, for example growth properties and/or stress tolerance. Accordingly, provided herein are transgenic plants overly expressing a RePRP as described herein, vectors for expressing the RePRP, methods for making the transgenic plants, and methods for improving growth properties or stress tolerance of plants by over-expressing a RePRP protein.

I. Repetitive Proline-Rich Proteins (RePRPs)

Repetitive Proline-rich Proteins (RePRPs) are ABA induced glycoproteins in plants. These proteins include a signal peptide at the N-terminus followed by a Proline-rich domain occupying about 70% of the protein. The Proline-rich domain contains numerous repetitive $PX_1PX_2$ motifs (SEQ ID NO: 25) and constitutes the hydrophilic regions, wherein P is a proline residue and $X_1$ and $X_2$ are any amino acid residues other than proline and more particularly are highly glycosylated with arabinose and glucose on multiple hydroproline residues converted from proline. The motif can be repeated "n" times, represented by $(PX_1PX_2)n$, for which it is understood that $X_1$ or $X_2$ can be the same or different in each repeat and the identifies of $X_1$ or $X_2$ residue are not necessarily preserved throughout the "n" repeats of the residue. It is further understood that each of the repeats can be connected end to end (directly), or with one or more intervening amino acid(s) (indirectly). In some embodiments, n is an integer of 20 or more, 30 or more, 40 or more, 50 or more, 60 or more, 70 or more, or 80 or more. In some embodiments, RePRPs have a content of proline e.g 20% or more, 30% or more, 40% or more, 50% or more based on the total number of the amino acid residues of this protein. In some embodiments, $X_1$ or $X_2$ is selected from the group consisting of lysine (Lys, K), glutamate (Glu, E), Asparagine (Asn, N), Aspartate (Asp, D), tyrosine (Tyr, Y), valine (Val, V), Histidine (His, H), isoleucine (Ile, I), glycine (Gly, G), threonine (Thr, T), glutamine (Gln, Q), serine (Ser, S). In some embodiments, RePRPs have 200 to 500 amino acids in length e.g. about 200, 250, 300 or 350 amino acid in length.

According to the present disclosure, the terms "polypeptide," "peptide" and "protein" as used herein refer to a polymer formed of amino acid residues, wherein one or more amino acid residues are naturally occurring amino acids or artificial chemical mimics.

The RePRPs described herein can be a naturally occurring protein of any suitable species. Exemplary RePRPs may be from plants preferably from monocot plants, including, but not limited to, rice, barley, wheat, maize and sorghum. In rice, there are two subclasses of RePRPs, (1) RePRP1 including RePRP1.1 (SEQ ID NO: 1) and RePRP1.2 (SEQ ID NO: 2) and (2) RePRP2, including RePRP2.1 (SEQ ID NO: 3) and RePRP2.2 (SEQ ID NO: 4).

In some embodiments, the RePRPs may comprise the amino acid sequence of SEQ ID NO: 1, 2, 3 or 4. Alternatively, the RePRPs may be a naturally occurring protein that is highly homologous to SEQ ID NO: 1, 2, 3 or 4, for example, sharing at least 85% sequence identity in the entire length (e.g., at least 90%, at least 93%, at least 95%, or at least 97%). Such RePRPs can be readily identified from publically available gene database (e.g., GenBank) using SEQ ID NO: 1, 2, 3 or 4 as a query.

It is understandable a polypeptide may have a limited number of changes or modifications that may be made within a certain portion of the polypeptide irrelevant to its activity or function and still result in a molecule with an acceptable level of equivalent biological activity or function. Modifications and changes may be made in the structure of such polypeptides and still obtain a molecule having similar or desirable characteristics. For example, certain amino acids may be substituted for other amino acids in the peptide/polypeptide structure (other than the conserved region) without appreciable loss of activity. Amino acid substitutions are generally based on the relative similarity of the amino acid side-chain substituents, for example, their hydrophobicity, hydrophilicity, charge, size, and the like. For example, arginine (Arg), lysine (Lys), and histidine (His) are all positively charged residues; and alanine (Ala), glycine (Gly) and serine (Ser) are all in a similar size. Therefore, based upon these considerations, arginine (Arg), lysine (Lys) and histidine (His); and alanine (Ala), glycine (Gly) and serine (Ser) may be defined as biologically functional equivalents. One can readily design and prepare recombinant genes for microbial expression of polypeptides having equivalent amino acid residues.

Therefore, in some embodiments, the RePRPs can be a functional variant of a naturally occurring RePRP. Such a functional variant may share a high sequence identity with the wild-type counterpart, for example, at least 85% (e.g., 90%, 95%, 96%, 97%, 98% or 99%) sequence identify to the amino acid sequence of the wild-type counterpart and possess substantially similar bioactivities as the wild-type counterpart.

To determine the percent identity of two amino acid sequences, the sequences can be aligned for optimal comparison purposes (e.g., gaps can be introduced in the sequence of a first amino acid sequence for optimal alignment with a second amino acid sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

II. Vectors Encoding RePRPs

In some aspects, the present invention provides vectors comprising a nucleic acid encoding any of the RePRPs described herein. The term "nucleic acid" or "polynucleotide" refers to a polymer composed of nucleotide units, including naturally occurring deoxyribonucleic acid ("DNA") and ribonucleic acid ("RNA") as well as any analogs thereof. Polynucleotides can be synthesized, for example, using an automated DNA synthesizer. The term "nucleic acid" typically refers to relatively larger polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

In some embodiments, a nucleic acid encoding a RePRP protein as described herein is SEQ ID NO: 5 (encoding OsRePRP1.1), SEQ ID NO: 6 (encoding OsRePRP1.2), SEQ ID NO: 7 (encoding OsRePRP2.1), or SEQ ID NO: 8 (encoding OsRePRP2.2).

A "vector," as used herein, can be a recombinant nucleic acid-based vehicle to artificially carry foreign genetic material into a host cell, in which the foreign genetic material can be replicated and/or expressed. The vector as described herein may be a cloning and/or an expression vector. The vector may be in linear or circular form. It may remain episomal or integrate into the host cell genome when introduced into a host cell. In some embodiments, the vector can be a viral vector or a non-viral vector (e.g., a plasmid). In particularly examples, the vectors may be plant vectors or *Agrobacterium* vectors."

In some embodiments, the nucleic acid encoding a RePRP protein can be operably linked to a promoter in the vector to drive expression of RePRP either in vitro or in vivo. As used herein, the term "operably linked" may mean that a polynucleotide is linked to an expression control sequence e.g. a promoter in such a manner to enable expression of the polynucleotide when a proper molecule (such as a transcriptional factor) is bound to the expression control sequence. As used herein, the term "expression control sequence" or "regulatory sequence" means a DNA sequence that regulates the expression of the operably linked nucleic acid sequence in a certain host cell.

Examples of vectors include, but are not limited to, plasmids, cosmids, phages, YACs or PACs. Typically, in vectors, the given nucleotide sequence is operably linked to the regulatory sequence such that when the vectors are introduced into a host cell, the given nucleotide sequence can be expressed in the host cell under the control of the regulatory sequence. The regulatory sequence may comprises, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, an operator sequence, a secretion signal sequence (e.g., alpha-mating factor signal) and other control sequence (e.g., Shine-Dalgano sequences and termination sequences). Preferably, vectors may further contain a marker sequence (e.g., an antibiotic resistant marker sequence) for the subsequent screening/selection procedure.

In some examples, the promoter described herein may be heterologous to the nucleic acid encoding the RePRP in the vector. As used herein, a promoter heterologous to a coding sequence (a gene) refers to a promoter that is not the natural promoter that controls (drives) expression of the gene in native state. For example, the vector of the present disclosure may comprise a promoter derived from a non-RePRP gene.

In some instances, the promoter described herein can be constitutive, which initiates transcription independent of the influence of regulation. Exemplary constitutive promoters include, but are not limited to a maize ubiquitin (Ubi) promoter, a rice actin (Actl) promoter, and a cauliflower mosaic virus 35S (CaMV35S) promoter.

In other instances, the promoter described herein can be inducible, which initiates transcription in a regulated manner, for example, in the presence or absence of a particular factor. Exemplary inducible promoters include an ethanol inducible promoter (e.g., a AlcR/AlcA promoter) or a β-estradiol inducible promoter (e.g., a XVE promoter, see Examples section below). Exemplary promoters inducible by biotic or abiotic stress (e.g., osmotic stress, drought stress, salt stress, high or low temperatures, hypoxia, anoxia, hydration, pH, chemicals, hormones or a combination thereof) include an *Arabidopsis* rd29A promoter, an *Arabidopsis* corl SA promoter, an *Arabidopsis* kinl promoter, an *Arabidopsis* heat-shock factor (HSF) promoter, an alpha-amylase promoter, and a synthetic ABRC321 promoter.

In certain embodiments, a promoter sequence as used in the invention is a synthetic ABRC321 promoter, having SEQ ID NO: 9 (1xABRC321), SEQ ID NO: 10 (2xABRC321) or SEQ ID NO: 11 (3xABRC321), preferably SEQ ID NO: 11 (3xABRC321)

In some embodiments, a vector comprising a nucleic acid encoding a RePRP protein operably linked to a promoter comprises a fused promoter/coding region fragment of SEQ ID NO: 12 (Ubi:OsRePRP2.1).

In some embodiments, a vector comprising a nucleic acid encoding a RePRP protein operably linked to a promoter comprises a fused promoter/coding region fragment of SEQ ID NO: 13 (3xABRC321i:OsRePRP2.1).

In some embodiments, a vector comprising a nucleic acid encoding a RePRP protein operably linked to a promoter comprises a fused promoter/coding resin fragment of SEQ ID NO: 14 (35S:OsRePRP2.1)

Any of the vectors described herein may be prepared via conventional recombinant technology.

III. Host Cells, Transgenic Plants, and Methods for Making Them

Some aspects of the present invention provide host cells (e.g., an *Agrobacterium* cell or a plant cell) comprising any of the vectors as described herein. These host cells (or called recombinant cells) carry exogenous/foreign genetic materials (e.g., the vectors described herein), which can be introduced into the host cell via conventional practice. "Exogenous genetic materials" as used herein can mean that the genetic materials are not originally present in the cells and instead artificially introduced into the cells of a parent thereof. In some instances, the exogenous genetic material may be derived from a different species as the host cell. In some other instances, the exogenous genetic material may be derived from the same species as the host cell and introduced into the host cell such that the resultant recombinant cell comprises extra copies of the genetic material as compared with the wild-type counterpart. The term "transformation" or "transform" as used herein refers to the introduction of exogenous genetic materials into a host cell such as a plant cell.

In certain embodiments, the host cell may be an *Agrobacterium* host cell. In certain embodiments, the host cell may be a plant cell, for example, a cell from a monocotyledonous plant or a dicotyledonous plant.

Suitable conventional methods are available to make the recombinant cells described herein. Examples of such methods include electroporation, PEG operation, particle bombardment, micro injection of plant cell protoplasts or embryogenic callus or other plant tissue, or *Agrobacterium*-mediated transformation.

RePRP expression (e.g., before and after transformation of a vector presented herein in a host cell) may be detected using methods known in the art. For example, reverse transcriptional polymerase chain reaction (RT-PCR) may be used to determine RePRP mRNA expression. Additional detection methods include western blot analysis and an enzyme-linked immunosorbent assay (ELISA) with an anti-RePRP antibody for protein detection.

The present invention also provides a transgenic plant comprising an exogenous nucleic acid operably linked to a promoter, wherein the exogenous nucleic acid (a transgene) encodes any of the RePRPs as described herein.

As used herein, plants may be a full plant or a part thereof, including a fruit, shoot, stem, root, leaf or seed, or various types of cells in culture (e.g., single cells, protoplasts, embryos, callus, protocorm-like bodies, and other types of cells). As described above, a plant of the present disclosure may be a monocot or a dicot.

In some embodiments, the plants as described herein are monocotyledonous plants. Examples of monocots include, but are not limited to, rice, barley, wheat, rye, oat, corn, bamboo, sugarcane, onion, leek and ginger.

In other embodiments, the plants described herein are dicotyledonous plants. Exemplary dicot plants include *Arabidopsis*, soybean, peanut, sunflower, safflower, cotton, tobacco, tomato, pea, chickpea, pigeon pea and potato.

A variety of procedures that can be used to engineer a stable transgenic plant are available in this art. In one embodiment of the present invention, the transgenic plant is produced by transforming a tissue of a plant, such as a protoplast or leaf-disc of the plant, with a recombinant *Agrobacterium* cell comprising a nucleic acid encoding a desired protein (e.g. RePRPs) and generating a whole plant from the transformed plant tissue. In another embodiment, a nucleic acid encoding a desired protein can be introduced into a plant via gene gun technology, particularly if transformation with a recombinant *Agrobacterium* cell is not efficient in the plant.

Specifically, a "transgenic plant" described herein can refer to a plant that comprises a transgene (such as an exogenous nucleic acid comprising a RePRP gene operably linked to a suitable promoter) allowing for expression of a RePRP gene in the transgenic plant.

In some embodiments, the transgenic plants, described herein, overexpress RePRPs. As used herein, the term "overexpression" can refer to the production of a gene product (e.g. RePRPs) in transgenic plants that exceeds levels of production in non-transgenic (wild type) counterpart plants, including but not limited to constitutive or induced expression. For example, the level of the RePRPs in the transgenic plant may be at least 10% higher (e.g., 20% higher, 30% higher, 50% higher, 1-fold higher, 2-fold higher, 5-folder higher, 10-fold higher, or above) as compared with that in non-transgenic (wild type) counterpart plants. In some instances, the wild-type parent does not express the RePRPs.

According to the present invention, a transgenic plant as disclosed herein may exhibit improved stress tolerance (e.g., biotic stress or abiotic stress). Biotic stress can be stress that occurs as a result of damage done to plants by other living organisms, such as pathogens e.g. bacteria, viruses, fungi, parasites, beneficial and harmful insects. Abiotic stress can be the negative impact of non-living factors on the living organisms in a specific environment. In some embodiments, the abiotic stress is osmotic stress, drought stress, salt stress, or a combination thereof.

In some embodiments, improving the stress tolerance of a plant refers to increasing the ability of a plant to survive under stress. For example, the survival rate of a transgenic plant as disclosed herein may be at least 20% higher (e.g., 30% higher, 50% higher, 1-fold higher, 2-fold higher, 5-folder higher, 10-fold higher, 20-fold higher, 50-fold higher, 100-folder higher, or above) than the survival rate of its wild-type counterpart, under stress and/or during recovery from stress.

In some embodiments, a transgenic plant as disclosed herein exhibits substantially no growth reduction compared to its wild-type counterpart under the same condition. In other words, the presence of the transgene can have no substantial detriment effects in plant growth. For example, plant height, panicle length, panicle numbers or root number/length of a transgenic plant as disclosed herein may be less than 15% (e.g. less than 10%, less than 5% or below) reduction or unaffected (maintained the same) than that of its wild-type counterpart under the same growth condition.

In some embodiments, a transgenic plant as disclosed herein exhibits substantially no yield reduction under stress and/or during recovery from stress, compared to normal, non-stress conditions. For example, grain yield reduction of a transgenic plant as disclosed herein may be less than 15% (e.g. less than 10%, less than 5% or below) under stress and/or during recovery from stress, compared to normal, non-stress conditions. In particular, the yield reduction of the transgenic plant of the present invention, under stress and/or during recovery from stress versus normal, non-stress conditions, is less than that of its wild-type counterpart.

In some embodiments, a transgenic plant as disclosed herein may exhibit improved ability to survive under salt stress. Salt stress may be mimicked by exposure to sodium chloride (NaCl) at 100 mM or higher (e.g. 150 mM or higher, 200 mM or higher, 250 mM or higher). In some embodiments, plants may be allowed to recover from salt stress.

In some embodiments, a transgenic plant as disclosed herein may exhibit is improved ability to survive under osmotic stress. Osmotic stress may be mimicked by exposure to polyethylene glycol (PEG) at 20% or higher (e.g. 30% or higher). In some embodiments, osmotic stress is mimicked under 30% PEG6000. In some embodiments, plants may be allowed to recover from osmotic stress.

In some embodiments, a transgenic plant as disclosed herein may exhibit improved ability to survive under drought stress. Drought stress may be mimicked by dehydration. In some embodiments, recovery from drought stress may be achieved through rehydration.

Accordingly, the present invention also provides methods of producing the transgenic plants described herein. The method may comprise: (a) transforming a plant cell with a nucleic acid operably linked to a promoter to obtain a recombinant plant cell expressing a RePRP protein, wherein the nucleic acid encodes the RePRP protein; and (b) growing the recombinant plant cell obtained in (a) to generate the transgenic plant.

The present invention further provides methods for improving growth (e.g., under stress and/or during recovery from stress) or stress tolerance of a plant. The method may comprise: (a) transforming plant cells with a vector comprising a nucleic acid operably linked to a promoter to obtain recombinant plant cells expressing a RePRP protein, wherein the nucleic acid encodes the RePRP protein; (b) growing the recombinant plant cells obtained in (a) to generate a plurality of transgenic plants; and (c) selecting a transgenic plant from the plurality of transgenic plants generated in (b) that exhibits an improved feature in respect of stress tolerance or growth as described herein, including a higher survival rate to abiotic stress, substantially no growth reduction, or a combination thereof, as compared with a non-transgenic plant counterpart growing under the same condition. In some embodiments, the transgenic plant as selected is that exhibits substantially no growth/yield reduction under stress, compared to normal, non-stress conditions. In some embodiments, the transgenic plant as selected is that exhibits similar growth features and/or less yield reduction under stress compared to its non-transgenic plant counterpart.

Without further elaboration, it is believed that one skilled in the art can, based on the disclosure herein, utilize the present invention to its fullest extent. The following specific examples are, therefore, to be construed as merely descriptive, and not limitative of the remainder of the disclosure in any way whatsoever.

EXAMPLES

In this study, we generated OsRePRP2.1 over-expressing transgenic plants and found that OsRePRP2.1 over-expression makes plants more tolerant to drought and salinity conditions. In the field test with semi-drought conditions, OsRePRP2.1 over-expression lines also showed no substantial growth retardation and less reduction in grain yield than that in wild type plants. In order to further reduce yield penalty in the OsRePRP2.1 over-expression plants, stress-induced expression of OsRePRP2.1 controlled by the synthetic 3XABRC321 promoter are introduced into transgenic rice. These transgenic plants with ABA/stress induced over-expression of OsRePRP2.1 show significantly higher drought tolerance level and maintain normal plant growth under non-stress conditions.

1. Materials and Methods 1.1 Plant Materials and Growth Conditions

Seeds of wild-type rice (*Oryza sativa* L., cv. Tainung 67; "TNG67") were sterilized with 2% sodium hypochloride for 30 min. and washed thoroughly with distilled water. To obtain uniform germination, rice seeds were soaked in distilled water at 37° C. for 1 day in darkness and then germinated in 20 cm petri dishes containing distilled water at 37° C.

Transgenic rice seeds were germinated in water containing hygromycin-B (30 μg/ml; Invitrogen) at 28° C. for 3 days to select for transgene containing seedlings. Uniformly germinated seeds were then selected and cultivated in a beaker containing half-strength Kimura B solution (Hsu et al., 2003). The hydroponically cultivated seedlings were grown at 28° C. at 90% relative humidity in 14 h light/10 h dark conditions with a light intensity of 100~105 μmol photons $m^{-2}$ $sec^{-1}$).

*Arabidopsis* seeds were sterilized with 0.6% sodium hydrochloride for 15 mins and washed thoroughly with distilled water. To select transgene containing plants, seeds were sown on half strength of Murashige and Skoog (MS) medium with 1% sucrose and 0.8% agar (pH5.7) with kanamycin (50 µg/ml; Invitrogena) at 4° C. in the darkness for 2 days, and then grew on plates at 22° C. in 16 hr light/8 hr dark cycle for 5 days. Homozygous transgenic plants and wild-type seeds grew on the normal half strength of MS medium with 1% sucrose and 0.8% agar (pH5.7) without antibiotics for 10 days and transferred to soil conditions for the phenotype observation.

1.2 Generation of Transgenic Plants

OsRePRP2.1 over-expressing transgenic rice were generated as follows. The OsRePRP2.1 coding region amplified by genomic PCR was cloned behind the maize Ubi1 promoter with its first intron in the pPZP binary vector. This vector contains a combined promoter/coding region fragment of SEQ ID NO: 12 (Ubi:OsRePRP2.1). Transgenic rice lines were generated with this construct via *Agrobacterium*-mediated transformation essentially as described in Hong et al., 2004, in the rice transformation laboratory at the Institute of Molecular Biology, Academia Sinica, Taiwan.

OsRePRP2.1 over-expressing transgenic *Arabidopsis* plants were generated as follows. The OsRePRP2.1 coding region was clones behind the 35S promoter in the pKGW vector. The vector contains a combined promoter/coding region fragment of SEQ ID: 14 (35S:OsRePRP2.1). Transgenic *Arabidopsis* plants were generated with this construct via *Agrobacterium*-mediated vacuum infiltration transformation performed in Transgenic Plant Laboratory, Academia Sinica, Taiwan OsRePRP-RNAi knockdown lines were generated as follows. The coding regions of the OsRePRP1.1 and 2.1 genes were amplified by genomic PCR and fused together in pCR8/GW/TOPO (Invitrogen). The combined fragment was excised and cloned into the pANDA binary vector described in Miki et al., 2004 via LR recombination (LR Clonase, Invitrogen). Transgenic lines were obtained from this construct as described in the preceding paragraph.

A stress-inducible OsRePRP2.1 construct was obtained by fusing the OsRePRP2.1 coding region to the 3XABRC321 promoter (SEQ ID NO: 7) (Chen et al., 2015) in the pENTR vector (Invitrogen). The combined promoter/coding region fragment was cloned into the pZP200 binary vector by LR recombination. This vector contains a combined promoter/coding region fragment of SEQ ID NO: 13 (3XABRC321:OsRePRP2.1). Again, transgenic plants were generated via *Agrobacterium*-mediated transformation.

1.3 RT-PCR Analysis

For the determination of OsRePRP transcript levels, total RNA was isolated from rice tissues using TRIzol reagent (Invitrogen) according to the supplier's recommendations. First-strand cDNA was synthesized using the SuperScript II first-strand synthesis system (Invitrogen). Gene specific primer sets used for RT-PCR to quantify OsRePRP gene expression are provided in Table 1 below. The rice OsActin gene was used as an internal control.

TABLE 1

RT-PCR Primers RT-PCR analysis

| Gene | Primer | Sequence (5' to 3') |
|---|---|---|
| OsRePRP1.1 | Forward | ACAAGCTCACAGTTCAGTTACGTACAAC (SEQ ID NO: 15) |
| | Reverse | GCGCTCCTTCCTCGGGT (SEQ ID NO: 16) |
| OsRePRP1.2 | Forward | GATCACAGAAGCTCACAGTTCAGTT (SEQ ID NO: 17) |
| | Reverse | TGACTCGCTCGCTCCTCC (SEQ ID NO: 18) |
| OsRePRP2.1 | Forward | ATGAGGAGATCAATCCTCTCACTG (SEQ ID NO: 19) |
| | Reverse | TCAGTTCCCGGGCACAATTATAG (SEQ ID NO: 20) |
| OsRePRP2.2 | Forward | AATGTTCCTGATCACATTGCCAAT (SEQ ID NO: 21) |
| | Reverse | CATACCAAAACTATGCGGAATCAT (SEQ ID NO: 22) |
| OsActin | Forward | CTGATGGACAGGTTATCACC (SEQ ID NO: 23) |
| | Reverse | CAGGTAGCAATAGGTATTACAG (SEQ ID NO: 24) |

1.4 Stress Treatments

For hydroponic system growth, wild type (TNG67) and transgenic plants (10 seedlings for each line) were grown in the same pot for 2 weeks under normal half-strength Kimura B solution. Two-week old seedlings (three-leaf old) were exposed to (i) 30% PEG in water (PEG 6000; Merck) for 18-20 hours, or (ii) 250 mM NaCl in half-strength Kimura B solution for 5 days. Seedlings were recovered in normal half-strength Kimura B solution for 10-12 days, followed by an evaluation of plant survival rate.

For growth in soil, seven 2-day germinated seeds per pot were grown in a soil mixture of 1:1 v/v clay and vermiculite for two weeks. Watering of two-week old seedlings (three-leaf old) was withheld for 12-14 days, and plants were then re-watered for 12 days before pictures were taken and survival rates were measured.

2. Results 2.1 OsRePRP2.1 Over-Expression Enhances Tolerance to High Salinity and Dehydration Multiple stably transformed lines were generated that overexpress the OsRePRP2.1 gene ("OsRePRP2.1OX"). Ectopic expression of this gene was controlled by the maize ubiquitin promoter. These stably transformed lines are already in T4 generation of homozygous plants. The transcript levels of several OsRePRP genes in roots from these lines were quantified by RT-PCR using the primers shown in Table 1 above.

The results are shown in Table 2 below.

TABLE 2

Relative mRNA expression of OsRePRP transformed rice lines

| endogenous | TNG67 | | OsRePRP2.1OX | | |
|---|---|---|---|---|---|
| | normal | salt treated | #2 | #10 | #19 |
| OsRePRP2.1 | 1 | 1.9 | 2.0 | 2.1 | 1.9 |
| OsRePRP2.2 | 1 | 1.5 | 1.4 | 1.2 | 1.3 |
| OsRePRP1.1 | 1 | 1.6 | 1.1 | 1.2 | 1.0 |
| OsRePRP1.2 | 1 | 1.2 | 0.9 | 0.9 | 0.9 |

OsRePRP2.1 transcript levels were significantly higher in over-expression lines, as compared to those in wild type TNG67 plants under normal condition. The expression level of OsRePRP2.1 induced by salt treatment in TNG67 plants was similar to that observed in untreated OsRePRP2.1 over-expression lines. The expression level of OsRePRP2.2, OsRePRP 1.1 and OsRePRP 1.2 was not significantly affected by overexpression of OsRePRP21.

2.2 OsRePRP2.1 Over-Expression Enhances Tolerance to High Salinity

The transgenic rice plants described above were tested for their response to high salinity conditions in order to determine whether OsRePRP-mediated root architecture adjustments were beneficial to rice plants under stress. Ten individual plants of each transgenic line were grown side by side with and TNG67 plants in a hydroponic culture chamber. Three-leaf old plants were treated with 250 mM NaCl for five days, and then moved to normal culture medium for a 12 day recovery period. After the recovery period, the survival rate of each line was compared to that of TNG67. The results indicated that three independent OsRePRP2.1OX transgenic rice plants had a 25~40% survival rate, as compared to less than 5% for TNG67. See FIG. 1. Clearly, OsRePRP2.1 over-expression enhances rice plant adaptation to salinity conditions.

2.3 OsRePRP2.1 Over-Expression Enhances Tolerance to Dehydration

Figure 2:
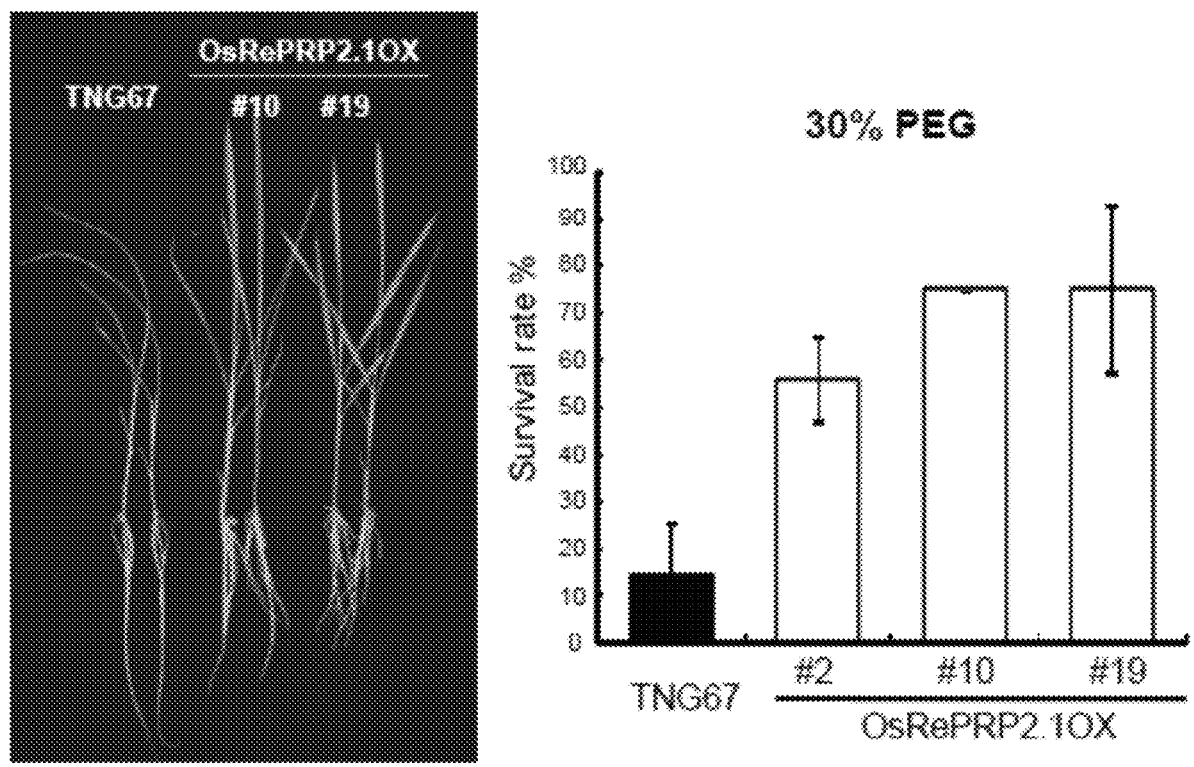
FIG. 2 shows that OsRePRP2.1 over-expression in rice enhanced drought tolerance. Three-leaf old seedlings were treated with 30% PEG for 20 hours, and then recovered to normal condition for 10 days. The survival rate of OsRePRP2.1OX transgenic plants was significantly higher than that of TNG67. Data are means ±SD from three experimental repeats.

In addition to salinity, water deficit, i.e., dehydration, is another important environment stress inhibiting rice plant growth. Dehydration was mimicked by treating rice plants with 30% PEG for 20 h. More specifically, three-leaf old plants were treated with 30% PEG for 20 h and then switched to normal culture medium for recovery. Survival rate was determined after 10 days of recovery. The results showed that three independent OsRePRP2.1OX transgenic rice plants had survival rates as high as 75%, as compared to only 15% in TNG67 wild-type plants. See FIG. 2. Furthermore, when the PEG treatment time was reduced to 16 hours, the shrunken leaves of OsRePRP2.1OX transgenic rice plants were able to fully expand in just one day after recovery and survival rate went up to 95%.

2.4 OsRePRP2.1 Over-Expression Enhances Tolerance to Drought Conditions

Figure 3:
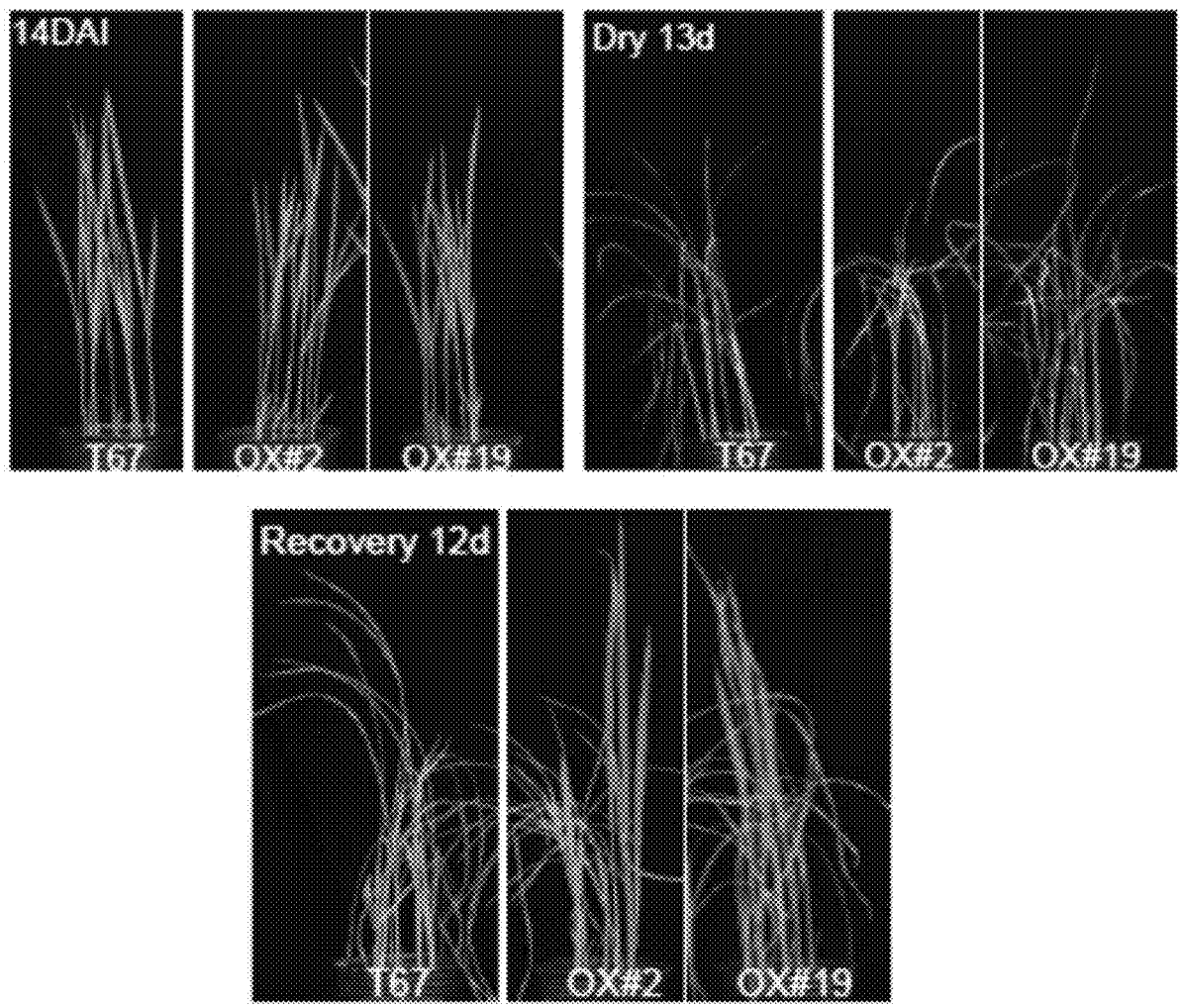
FIG. 3 shows that OsRePRP2.1 over-expression in rice enhanced the plant recovery after drought treatment. Watering of two-week old plants was withheld for 13 days, and watering was then reassumed for 12 days. Half of OsRePRP2.1OX plants survived and grew new leaves, while a few TNG67 plants survived.

When grown in soil, the OsRePRP2.1OX transgenic rice plants also showed high recovery rates after 13 days of withholding water in compared to no WT plants recovered. See FIG. 3. According to these results of abiotic stress tests, the ABA/stress induced OsRePRP family not only modulated root growth but was also involved in the stress tolerance processes.

2.5 RNA Interference ("RNAi")-Mediated Knockdown of OsRePRP Expression Reduces Stress Tolerance in Rice OsRePRP RNAi transgenic rice lines were generated to reduce the expression of all four OsRePRP genes. Rice OsRePRP family transcripts were determined by RT-PCR in salt treated roots of OsRePRP RNAi lines as described above. The results are shown in Table 3 below.

TABLE 3

Relative RePRP Gene expression in RNAi knockdown lines

| endogenous | TNG67 | | OsRePRP RNAi, salt treated | | | |
|---|---|---|---|---|---|---|
| | normal | salt treated | #3 | #5 | #6 | #7 |
| OsRePRP1.1 | 1 | 1.56 | 0.69 | 0.04 | 0.08 | 0.18 |
| OsRePRP1.2 | 1 | 1.18 | 0.76 | 0.21 | 0.47 | 0.54 |
| OsRePRP2.1 | 1 | 3.26 | 1.97 | 0.08 | 0.14 | 0.80 |
| OsRePRP2.2 | 1 | 1.42 | 0.71 | 0.02 | 0.09 | 0.33 |

The four OsRePRP RNAi lines tested each showed significantly lower levels of RNA transcripts of the endogenous OsRePRP1.1, OsRePRP1.2, OsRePRP2.1, and OsRePRP2.2 genes, even after salt treatment.

2.6 OsRePRP Knock-Down Transgenic Rice Plants are Sensitive to Salinity and Drought Conditions OsRePRP RNAi transgenic rice plants were tested for their sensitivities to salt and to PEG as described above. In the salinity test (250 mM NaCl), the average survival rate of RNAi lines was 3.2%, less than half of the 9.1% displayed by wild-type TNG67 plants. Under the same conditions, OsRePRP2.1OX transgenic plants had a survival rate of as high as 80%.

Figure 4:
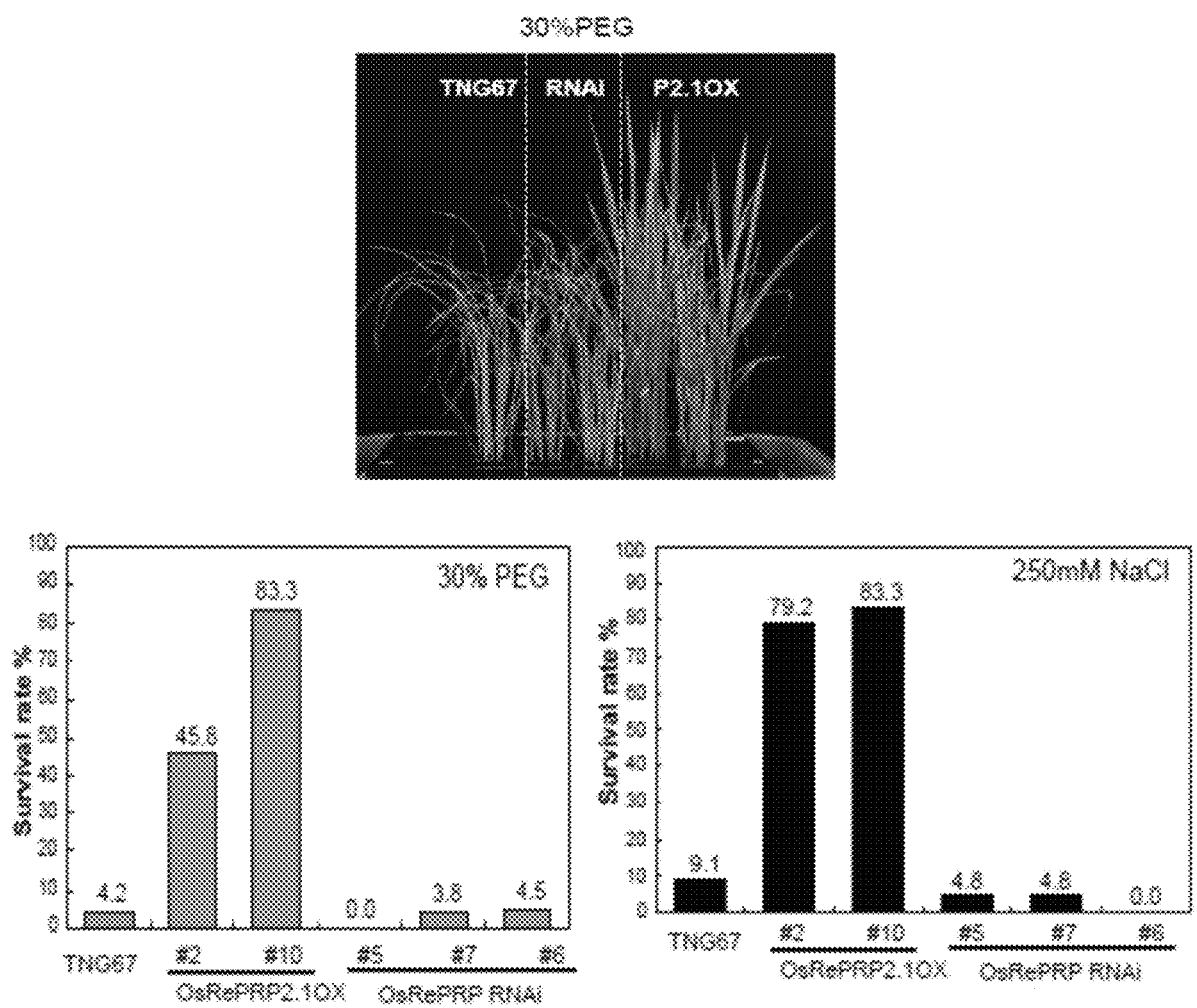
FIG. 4 shows that OsRePRP RNAi plants were sensitive to abiotic stress treatments. Three-leaf old seedlings were treated for 250 mM NaCl for 5 days or 30% PEG for 24 hours. The survival rate was recorded after 12 days of recovery. The average survival rate of RNAi lines was significantly lower than WT (TNG67) in both stress treatments, while OsRePRP2.1 over-expression lines showed up to 80% survival rate.

Turning to the drought test (30% PEG), the average survival rate of RNAi lines, i.e., 2.7%, was lower than the 4.2% survival rate of TNG67 plants. Under the same conditions, between 45% and 83% of OsRePRP2.1OX transgenic rice plants survived. See FIG. 4. According to these results, knocking down expression of OsRePRP genes in rice led to greater sensitivity to salinity and drought treatments.

2.7 OsRePRP2.1 Overexpressing Transgenic Rice Plants are Tolerant to Drought Conditions in the Field Field drought tests were performed to evaluate the tolerance level of TNG67 wild-type and OsRePRP2.1OX transgenic plants. Field tests were performed twice in the first and second growing seasons of 2015. In these two seasons, OsRePRP2.1OX lines were grown side by side with TNG67 plants, with 24 individuals for each line grown with a spacing of 25×25 cm between each plant in an irrigated filed and in a non-irrigation field at the same time. Tests were initiated by transplanting 25-day old transgenic seedlings to the genetically modified organism-certified field at National Chung Hsing University, Taiwan, Normal irrigated conditions were achieved by flooding the field with 1-5 cm of water until the end of the active tilling stage, i.e., 60-70 days after imbibition, at which time the water was drained. Soil was kept moist until the end of tillering stage. The field was then flooded again with 3-10 cm of water until the milky stage, and then water was again drained.

In the non-irrigated field, soil was kept just moist instead of flooding during the entire planting period. Plant growth and grain yield were observed. The results are summarized in Table 4 below.

TABLE 4

Results of plant growth and grain yield reduction of OsRePRP overexpressing plants.

| | Plant growth | | | | | | |
|---|---|---|---|---|---|---|---|
| | Irrigated | | | Non-irrigated | | | |
| | Plant height(cm)[1] | Panicle length(cm)[1] | Panicle number[1] | Plant height(cm)[1] | Panicle length(cm)[1] | Panicle number[1] | Grain yield Loss %[2] |
| TNG67 | 101.6 ± 2.9 | 19.7 ± 2.1 | 11.3 ± 2.2 | 97.8 ± 3.3 | 19.5 ± 2.2 | 10.7 ± 2.2 | 15.0 |
| OX#2 | 105.2 ± 3.4 | 19.9 ± 2.4 | 10.9 ± 1.4 | 94.9 ± 5.9 | 19.7 ± 2.3 | 10.7 ± 2.6 | 5.3 |
| OX#10 | 103.4 ± 4.4 | 18.8 ± 2.3 | 10.6 ± 1.2 | 93.6 ± 5.7 | 17.8 ± 2.0 | 10.5 ± 1.9 | 4.2 |
| OX#19 | 101.2 ± 3.2 | 19.3 ± 2.4 | 11.1 ± 1.3 | 94.0 ± 4.5 | 19.4 ± 2.3 | 9.2 ± 1.9 | 13.6 |

[1]Plant height, panicle length and panicle number were measured for each individual of each line for two seasons in 2015 and shown as means ± SD (n = 24).
[2]Plant grain yield was measured for each individual of each line for two seasons in 2015. Grain yield loss (%) was shown as an average of two-season loss (%) of each line, wherein each season loss of each line was calculated as follows: (means of grain yield in irrigated condition − means of grain yield in non-irrigated condition)/means of grain yield in irrigated condition × 100 (%).

Figure 6A:
FIGS. 6A-6C show that OsRePRP2.1 over-expression in *Arabidopsis* plants grow normally, similar to non-transgenic *Arabidopsis* plants under normal conditions.
Figure 6B:
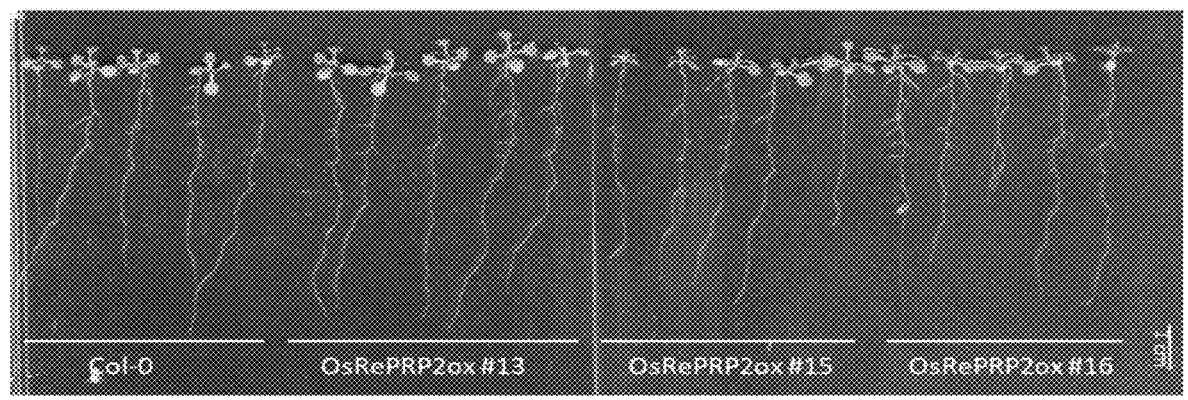
Figure 6C:
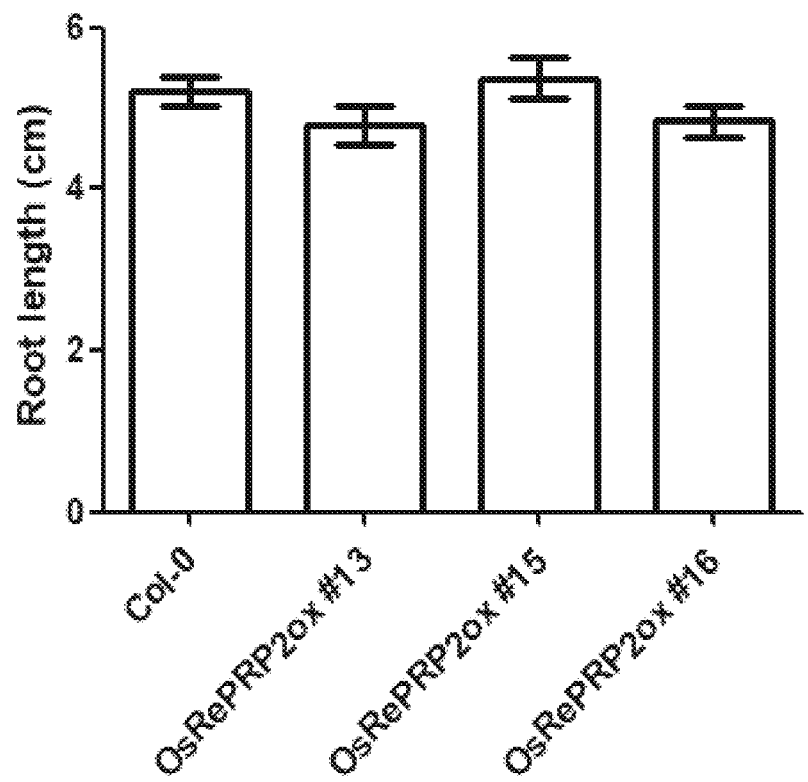

The results showed that plant height, panicle length, and panicle numbers were similar in OsRePRP2.1OX and TNG67 plants under normal irrigation conditions. In addition, OsRePRP2.1 overexpressing transgenic Arabidopsis plants were produced and the growth was found similar to non-transgenic Arabidopsis plant under normal conditions. See FIGS. 6A-6C. It shows that overexpression of OsRePRP2.1 does not affect the plant growth including plant height, panicle length, panicle number and root length.

On the other hand, TNG67 plants grown in non-irrigated filed caused grain yield loss of about 15% as compared to TNG67 plants grown in irrigated conditions. In contrast, OsRePRP2.1OX transgenic rice plants showed less than 15% reduction in rice yield when grown in non-irrigated filed as compared to OsRePRP2.1OX transgenic rice plants grown in irrigated conditions; among them, surprisingly, some lines (e.g. OX#2 and OX#10) exhibit very low grain loss, only about 5% loss. These observations suggest that over-expression of OsRePRP2.1 in rice helps plants survive and maintain near normal seed production under drought conditions.

2.8 Transgenic Rice Plants Having Stress-Induced Over-expression of OsRePRP2.1

Although constitutive expression of OsRePRP2.1 in rice enhanced drought tolerance level, over-expression also resulted in a yield penalty under non-stress conditions.

Rice plants were generated that contain a transgene containing OsRePRP2.1 controlled by a synthetic ABA/stress inducible promoter, 3XABRC321, which directs high level gene expression only under stress conditions (see Chen et al., 2015).

T1 and T2 plants were tested for drought tolerance in the PEG stress model mentioned above. After PEG treatment in hydroponic culture systems, 3 independent T2 rice plant lines carrying an inducible ABRC321:OsRePRP2.1 construct showed the significant higher survival rate as compared to wild type plants.

Figure 5A:
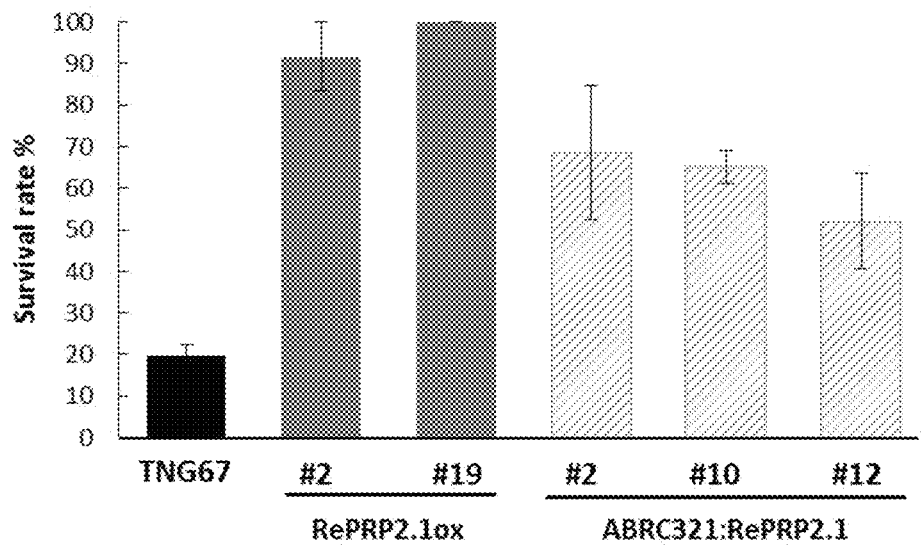
FIGS. 5A-5B show that induced expression of OsRePRP2.1 transgenic rice plants were tolerant to PEG treatment. Two-week old plants were treated with 30% PEG for 18 hours, then recovered to normal condition for 10 days.
Figure 5B:
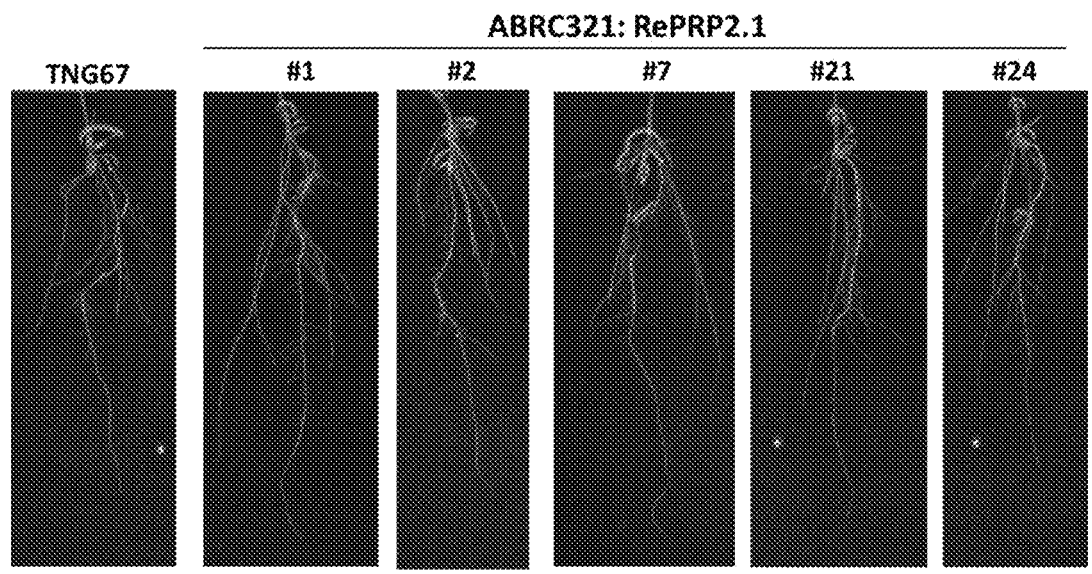

Furthermore, root growth inhibition in over-expression lines was not observed in induced expression lines. See FIGS. 5A-5B. Plant growth of ABRC321:OsRePRP2.1 transgenic plants also were not affected. Similar plant height, panicle length and panicle numbers of ABRC321:OsRePRP2.1 transgenic rice as those in wild type plants were observed under the normal condition. See Table 5.

TABLE 5

Results of plant growth of ABRC321:OsRePRP2.1 transgenic plants.

| | Plant height (cm) | Panicle length (cm) | Panicle numbers |
|---|---|---|---|
| TNG67 | 95.9 ± 3.3 | 18.5 ± 2.7 | 8.3 ± 1.4 |
| ABRC:P2.1#2 | 86.3 ± 3.3 | 16.6 ± 2.5 | 10.5 ± 2.0 |
| ABRC:P2.1#10 | 90.7 ± 3.8 | 17.8 ± 2.5 | 7.5 ± 1.9 |
| ABRC:P2.1#12 | 91.6 ± 4.8 | 17.5 ± 2.7 | 10.9 ± 1.6 |

1. Plant height, panicle length and panicle number were measured for each individual of each line in the first season of 2017 and shown as means ± SD (n = 15).

These results indicated that ABRC321:OsRePRP2.1 inducible transgenic rice plants were drought tolerant by virtue of OsRePRP2.1 expression. Yet, these plants did not suffer any growth retardation effects attributed to overexpression of OsRePRP2.1.

Given the above, the present invention provides technologies to improve stress tolerance and/or preventing growth reduction of a plant by introducing a polynucleotide encoding a Repetitive Proline-rich Protein (RePRP) into the plant. The invention helps plants not only to survive under stress but also maintain growth and productivity, which is beneficial to agricultural development.

The following references can be used to better understand the background of the application:
Boyer, J. S. (1982), Science 218, 443-448.
Chen et al (2015), Plant Biotechnology J. 13, 105-116.
Hong et al. (2004), Transgenic Research 13, 29-39.
Hsu et al. (2003), Plant, Cell Environment 26, 867-874.
Kar (2011), Plant Signaling Behavior 6, 1741-1745.
Miki et al. (2004), Plant Cell Physiology 45, 490-495.
Saab et al. (1990), Plant Physiology 93, 1329-1336.
Sharp et al. (2004), J. Experimental Botany 55, 2343-2351.
Tilman et al. (2002), Nature 418, 671-677.
Tseng et al. (2013), Plant Physiology 163, 118-134.
Xu et al. (2013), The New Phytologist 197, 139-150.

The contents of the above references are hereby incorporated by reference in their entirety.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present invention, and without departing from the spirit and scope thereof, can make various changes and modifications of the present invention to adapt it to various usages and conditions. Thus, other embodiments are also within the claims.

```
>OsRePRP1.1
                                                                (SEQ ID NO: 1)
MARRSPCLTAAVLLLGALAVASALVDEAAAAGQGLGHGARFMSKQGRAMYEKPPELEPKPKPKPHPKHESK

PEPKPEPKPEPKPYPEPKPETKPELKPEPKPNPEPKPEPKPEPKPEPKPYPEPKPKPKPEPKPEPKPEHKP

EPKPEPEPKPYPKPKPEPKPGPKPEPKPEPKPHPEPKPEPKPKPVPHPEPKPEPKPEPKPHPEPKPEPKPE

PKLHPKPEPKPHPEPEPKLKPEPKPEPKPEPEPKPEPKPEPKPEPKPYPKPKPEPKPVPKPKPIPHPGPKP

KPKPDPKLEPKPHPEPKPHPMPEPEPKPKPEPKPEPKPYPEPKPKLKPEPKPGPKPIAPPNKHKPPHMPPA

TNQ

>OsRePRP1.2
                                                                (SEQ ID NO: 2)
MARRSPCLAVAMLLLGALAVASAFIDEAAAAGRGLGHGARFMSKQGRVTYEKLPEPEPKPKPKPHPKPTPK

PEPKPEPEPKPVPEPEPKPEPKPEPKPEPKPEPKPYPEPKPEPKPEPKPEPEPKPEPKPEPKPEPKPYPEP

KPEPKPEPKPEPKPEPKPKPEPKPHPEPKPDPKPEPKPHPEPEPKPEPKPEPKPHPEPEPKPEPKPEPKPE

PKPEPKPEPKPKPKPEPKPKPEPKPYPEPKPKPEPKPEPKPEPKPEPKPEPKPEPKPEPKPEPKPKPEPKP

HPKPEPKPEPKPEPKPEPKPEPKPEPKPEPEPKPEPKPEPKPEPKPYPEPKPDPKPEPKPHPEPKPEPKPQ

PEPKPEPKPEPKPEPKPEPKPEPKPYPEPKPEPKPKPKPEPKPEAPPKKHKPPHIPPATDQ

>OsRePRP2.1
                                                                (SEQ ID NO: 3)
MRSILSLCFHLALAIALAANVPDHIANGRVIEAKSDPKPADPNPKPDPIPKPQPETKPSPQPNPQPNPQPD

PKPSPQPDPKPTPQPEPKQDPKPNPQPDPKPSPQPDPKPTPQPDPKQDPQPNPQPDPKPTPQPNPKQDPQP

NPQPDPKPTPQPDPKQDPQPNPQPSPKADPKPNPKPKPQPEPSPNPKPEPKPEPKPEPSPNPKPNPNPKPE

PQPDPKPEPKPQPEPSLPKPPPLSPAIAIIVPGN

>OsRePRP2.2
                                                                (SEQ ID NO: 4)
MRRSILSLCFHLALVIALAANVPDIANGRVIEAKSDPKPADPKPKPDPTPKPQPETKPSPQPNPQPNPQPD

PKPSPQPDPKPTPQPEPKQDPQPNPQPDPKQSPQPDPKPTPQPNPKQDPQPNPQPDPKPTLQPNPKQDPQP

NPQPNPKPTPQLDPKQDPQPNPQPSPKADPKPNPKPKPQPEPSPNPKPEPKPEPKPEPSPNPKPNPNPKPE

PQPDPKPEPKPQPEPSQPKLPPLSPAIAIIVPGN

>OsRePRP1.1
                                                                (SEQ ID NO: 5)
    1    caacagcaga  agtgagagag  ggagaagaag  ataagcgaag  aggaggagct  tagcttgcca 61    gccatggcta  ggcgctctcc  ttgcctcact  gccgccgtgc  tcctgcttgg  ggcattggcg 121    gtggcgagcg  ctttagttga  tgaagcggcg  gcagctggcc  agggactcgg  ccatggcgcc 181    cgcttcatga  gcaagcaggg  ccgtgcgatg  tacgagaagc  cgccagagct  ggagccgaag 241    ccaaagccaa  agcctcatcc  taagcatgaa  tcaaaaccgg  agccaaagcc  agaacctaag 301    ccggagccaa  agccataccc  agagccgaag  ccagagacga  aaccggagct  aaagccagaa 361    ccaaaaccta  atccagaacc  taaacctgag  cctaagcctg  aaccaaaacc  agaaccaaag 421    ccatacccag  agccgaagcc  aaagcccaaa  ccggagccaa  agccagaacc  aaaacctgag 481    cataaacctg  aaccaaaacc  agaaccagaa  ccaaagccat  acccaaagcc  aagccagag 541    ccaaaaccgg  ggcccaaacc  cgagccgaag  ccagagccta  agccacaccc  agaaccgaaa 601    ccggagccca  aaccaaagcc  agtgccacac  cctgaaccaa  aaccggaacc  aaagccggag 661    cccaaaccac  acccagaacc  aaagcctgag  ccgaaacccg  agcctaagct  acacccgaag 721    cctgagccaa  agccacaccc  agagcctgag  cctaagctta  aacctgaacc  aaaaccagag
```

-continued

```
 781   ccaaagccag agcctgaacc gaagcccgag ccaaagcctg aaccaaaacc agagcctaaa
 841   ccatatccaa agccaaaacc ggaacctaaa ccggtgccga agccgaagcc cattccacac
 901   ccaggaccaa aaccaaagcc taaacctgac ccaaagctag agcccaagcc acacccggag
 961   ccaaaaccac atccgatgcc tgaacctgaa ccaaagccta agcccgaacc aaagccagag
1021   cctaaaccat acccagaacc aaagcctaaa ctgaaacctg aacctaagcc tggaccgaaa
1081   cctatagcac cgccgaacaa gcacaagccg ccgcacatgc caccagcgac aaaccagtga
1141   cggcgatcgc tggagaccga gcatttgctg gctgcacggt tgaggcaccg acgacattat
1201   ttcacccgag gaaggagcgc tagcgagtca ctacactgta ccgtttctgg aataaagtga
1261   tgagctagct ttctgcttgc cttttctttt cctctcttat tttcctttta tttcatgttg
1321   gtttttcgga tgtgccactg ctagctagtg taattaaatt atttattatg tgcctaccgt
1381   cattttattt accgtgtctg tgacattcta ttgtctattg gcattattct cattgtaaaa
1441   tcttttggta atattatttg tcatcatttt tacccagctt ctaaaaaaaa aaa
```

>OsRePRP1.2
(SEQ ID NO: 6)
```
   1   atggcgaggc gctctccttg cctcgccgtc gccatgctcc tgcttggggc gttggcggtg
  61   gcgagcgcct tcattgatga agcggcggct gctggccggg ggctcggcca tggcgcccgc
 121   ttcatgagca agcagggtcg tgtgacatac gagaagctgc cggagccgga gccgaagcca
 181   aagccaaagc ctcatcctaa acccacgcca aaacctgagc ccaagccaga gccggagcca
 241   aaaccagtac ctgagcctga gcctaaaccg gaaccaaagc cagaaccaaa acctgagcct
 301   aagcctgaac ctaaaccata cccagagcca aaaccggagc cgaagccaga gccaaaacct
 361   gagccggagc ctaaacctga gcctaagcca gaaccaaaac cagaaccaaa gccgtaccca
 421   gagccgaagc cagagccaaa accggaaccg aagccggaac caaaaccgga gcccaaacca
 481   aagccagagc ccaaaccaca cccagaacca agcctgatcc gaaacctga gcctaagcca
 541   cacccagagc ctgagcctaa gcctgaacct aagcctgagc caagccaca ccctgagcct
 601   gaaccaaagc ctgagcctaa gcctgagcca agccagaac caaagccgga gccaaaacct
 661   gaaccaaaac caaagccaaa gccagagcca agccaaagc ctgagcccaa gccataccct
 721   gagcctaagc ctaagcctga accaaagcct gagcctaagc ctgagccaaa gccagaacca
 781   aagccggagc caaaacctga accaaaacca gagccaaagc cagagccaaa gccaaagcct
 841   gagcccaagc acacccctaa gcctgagcct aagcctgagc ccaagccaga accaaagcca
 901   gagccaaaac ctgaaccaaa accagagcca aaaccagagc ctgaaccgaa gcctgagcca
 961   aagcctgaac caaaaccaga gcccaaacca tatccagagc ctaaaccgga tcccaaacca
1021   gaacccaaac cacacccaga accaaagcca gagcccaagc cacagccgga gccaaaacca
1081   gagccgaagc ctgaacctaa accagagcct aagcccgaac caaaaccgga gcctaaacca
1141   tacccagagc caaagcctga accgaaacct aagcctaagc ctgagccaaa acctgaagca
1201   cctccgaaga agcacaagcc gccgcacata ccgccagcga ccgaccagtg a
```

OsRePRP2.1
(SEQ ID NO: 7)
```
   1   aacacaccta actaccacag cttgtgaact atcaagagtg agtagtagag tttgcagtga
  61   caacgagatg aggagatcaa tcctctcact gtgcttccat ttggcgcttg tcattgcatt
 121   ggcagcaaat gttcctgaca ttgccaatgg acgcgtgatt gaagctaaat ctgatccaaa
 181   gccagcagat cccaagccta aacctgaccc aacaccaaaa ccacaaccag agacaaagcc
 241   cagtccacag cctaaccctc aacctaaccc acagccagat ccaaaaccat caccgcagcc
 301   tgatccaaaa cctacaccac agcctgaacc aaaacaagat cctcaaccaa acccacagcc
```

```
 361   ggatccaaaa caatcgccgc agcctgaccc aaaacctaca ccacagccta acccaaaaca
 421   agatcctcaa ccgaacccac aacctgaccc aaaaccaacg ctgcaaccta acccaaaaca
 481   agatcctcag ccgaacccac agcctaaccc gaaaccaacg ccacagcttg acccgaaaca
 541   agatcctcaa ccgaacccac aacctagccc caaagctgac ccaaaaccaa atccaaagcc
 601   taagccacaa ccggagccga gcccaaatcc taagccggag ccaaaacctg aacccaaacc
 661   tgagccgagt cctaacccca agccaaatcc taatcccaag ccggagccac agcctgatcc
 721   taagccagaa cccaagcctc agccagagcc gtctcaacca agctgccac  cactttcacc
 781   agcaatagct ataattgtgc ccgggaactg agtagacttg gttgtttgct acgtatgatc
 841   ccgcatactt ttggtatgta ctattgctct agtgactatt tgtgtgtttt tcgtgtgttg
 901   ttcactagtg tgtccatgtg gctatctatg tgttttctta atgccgttgc atatgagcag
 961   gcgtgcttct tataataaag catacataca tacatacata catacataca tacatatata
1021   tatacacgtg tgttatgtat gtgcgtacat accatcaata aaagagcat  gtatccctgt
1081   gtgtcaat
```

>OsRePRP2.2
(SEQ ID NO: 8)
```
   1   aacacaccta gctaccacag cttgtgtact gtcaagagtg agtagtagag tttgtagtga
  61   caacgagatg agatcaatcc tctcactgtg cttccatttg gcgcttgcca ttgcattggc
 121   ggcaaatgtt cctgatcaca ttgccaatgg acgcgtgatt gaagctaaat ctgatccaaa
 181   gccagcagat cccaatccta aacctgaccc aacaccaaaa ccacaaccag agacaaagcc
 241   cagtccacag cctaaccctc aacctaaccc acagccagat ccaaaaccat caccgcagcc
 301   tgacccaaaa cctacaccac agcctgaaac aaaacaagat cctaaaccaa cccacaacc
 361   ggatccaaaa ccatctccgc agcctgaccc gaaacctaca ccacagcctg acccaaaaca
 421   agatcctcaa ccgaacccac aacctgaccc aaaaccaacg ccgcaaccta acccaaaaca
 481   agatcctcag ccgaacccac agcctgaccc aaaaccaacg ccacagcctg acccgaaaca
 541   agatcctcaa ccgaacccgc aacctagccc caaagctgac ccaaaaccaa atccaaagcc
 601   taagccacaa ccggagccga gcccaaatcc taagccggag ccaaagcctg aacccaaacc
 661   tgagccaagt cctaaccca  agccaaatcc taatcctaag ccggagccac agcctgatcc
 721   taagccagaa cccaagcctc agccagagcc atctctgcca agccaccac  ctctttcacc
 781   agcaatagct ataattgtgc ccgggaactg agtagacttt tgctacgta  tgattccgca
 841   tagttttggt atgtactatt gctctagtga ctatctatgt gtttgtcgtg tgttgttcac
 901   tggtgtatgt gtccatgtgg ctatctatgt gttttcttaa tgctgttgca tctgagcagg
 961   cgtgcttctt ataataaagc atatatatgc acgtgtgtta tgtatgtgcg tacatatata
1021   ccatgaataa aaagagcatg tatccctgtg tgtcact
```

>Synthetic promoter 1XABRC321
(SEQ ID NO: 9)
```
   1   ggtaccgcaa cgcgtgtcct ccctacgtgg cggctcgaga ttgccaccgg tctagagtcg
  61   actgcagcaa ttccggcatg ccgcagcaca ctataaatac ctggccagac acacaagctg
 121   aatgcatcag ttctccatcg tactcttcga gagcacagca agagag
```

>Synthetic promoter 2XABRC321
(SEQ ID NO: 10)
```
   1   ggtaccgcaa cgcgtgtcct ccctacgtgg cggctcgaga ttgccaccgg ggtaccgcaa
  61   cgcgtgtcct ccctacgtgg cggctcgaga ttgccaccgg tctagagtcg actgcagcaa
```

-continued

```
121    ttccggcatg ccgcagcaca ctataaatac ctggccagac acacaagctg aatgcatcag 181    ttctccatcg tactcttcga gagcacagca agagag
```

>Synthetic promoter 3XABRC321

(SEQ ID NO: 11)
```
  1    ggtaccgcaa cgcgtgtcct ccctacgtgg cggctcgaga ttgccaccgg ggtaccgcaa 61    cgcgtgtcct ccctacgtgg cggctcgaga ttgccaccgg ggtaccgcaa cgcgtgtcct 121    ccctacgtgg cggctcgaga ttgccaccgg tctagagtcg actgcagcaa ttccggcatg 181    ccgcagcaca ctataaatac ctggccagac acacaagctg aatgcatcag ttctccatcg 241    tactcttcga gagcacagca agagag
```

>Ubi:OsRePRP2.1

(SEQ ID NO: 12)
```
  1    ctgcagtgca gcgtgacccg gtcgtgcccc tctctagaga taatgagcat tgcatgtcta 61    agttataaaa aattaccaca tattttttt gtcacacttg tttgaagtgc agtttatcta 121    tctttataca tatatttaaa ctttactcta cgaataatat aatctatagt actacaataa 181    tatcagtgtt ttagagaatc atataaatga acagttagac atggtctaaa ggacaattga 241    gtattttgac aacaggactc tacagtttta tcttttttagt gtgcatgtgt tctccttttt 301    ttttttgcaa atagcttcac ctatataata cttcatccat tttattagta catccattta 361    gggtttaggg ttaatggttt ttatagacta atttttttag tacatctatt ttattctatt 421    ttagcctcta aattaagaaa actaaaactc tattttagtt tttttattta ataatttaga 481    tataaaatag aataaaataa agtgactaaa aattaaacaa atacccttta agaaattaaa 541    aaaactaagg aaacattttt cttgtttcga gtagataatg ccagcctgtt aaacgccgtc 601    gacgcagtct aacggacacc aaccagcgaa ccagcagcgt cgcgtcgggc caagcgaagc 661    agacggcacg gcatctctgt cgctgcctct ggaccctct cgagagttcc gctccaccgt 721    tggacttcgt ccgctgtcgg catccagaaa ttgcgtggcg gagcggcaga cgtgagccgg 781    cacggcaggc ggcctcctcc tcctctcacg gcaccggcag ctacggggga ttccttccc 841    accgctcctt cgctttccct tcctcgcccg ccgtaataaa tagacacccc ctccacaccc 901    tctttcccca acctcgtgtt gttcggagcg cacacacaca caaccagatc tcccccaaat 961    ccaccgtcg gcacctccgc ttcaaggtac gccgctcgtc ctccccccc ctctctacct 1021   tctctagatc ggcgttccgg tccatggtta gggcccggta gttctacttc tgttcatgtt 1081   tgtgttagat ccgtgtttgt gttagatccg tgctgctagc gttcgtacac ggatgcgacc 1141   tgtacgtcag acacgttctg attgctaact tgccagtgtt tctctttggg gaatcctggg 1201   atggctctag ccgttccgca gacgggatcg atttcatgat ttttttttgtt tcgttgcata 1261   gggtttggtt tgccccttttc ctttatttca atatatgccg tgcacttgtt tgtcgggtca 1321   tcttttcatg ctttttttttg tcttggttgt gatgatgtgg tctggttggg cggtcgttct 1381   agatcggagt agaattctgt ttcaaactac ctggtggatt tattaatttt ggatctgtat 1441   gtgtgtgcca tacatattca tagttacgaa ttgaagatga tggatggaaa tatcgatcta 1501   ggataggtat acatgttgat gcgggtttta ctgatgcata tacagagatg cttttgttcg 1561   cttggttgtg atgatgtggt gtggttgggc ggtcgttcat tcgttctaga tcggagtaga 1621   atactgtttc aaactacctg gtgtatttat taattttgga actgtatgtg tgtgtcatac 1681   atcttcatag ttacgagttt aagatggat gaaatatcga tctaggatag gtatacatgt 1741   tgatgtgggt tttactgatg catatacatg atggcatatg cagcatctat tcatatgctc 1801   taaccttgag tacctatcta ttataataaa caagtatgtt ttataattat tttgatcttg 1861   atatacttgg atgatggcat atgcagcagc tatatgtgga ttttttttagc cctgccttca
```

-continued

```
1921  tacgctattt atttgcttgg tactgtttct tttgtcgatg ctcaccctgt tgtttggtgt
1981  tacttctgca gatgaggaga tcaatcctct cactgtgctt ccatttggcg cttgtcattg
2041  cattggcagc aaatgttcct gacattgcca atggacgcgt gattgaagct aaatctgatc
2101  caaagccagc agatcccaag cctaaacctg acccaacacc aaaaccacaa ccagagacaa
2161  agcccagtcc acagcctaac cctcaaccta acccacagcc agatccaaaa ccatcaccgc
2221  agcctgatcc aaaacctaca ccacagcctg aaccaaaaca agatcctcaa ccaaacccac
2281  agccggatcc aaaacaatcg ccgcagcctg acccaaaacc tacaccacag cctaacccaa
2341  aacaagatcc tcaaccgaac ccacaacctg acccaaaacc aacgctgcaa cctaacccaa
2401  aacaagatcc tcagccgaac ccacagccta acccgaaacc aacgccacag cttgacccga
2461  aacaagatcc tcaaccgaac ccacaaccta gccccaaagc tgacccaaaa ccaaatccaa
2521  agcctaagcc acaaccggag ccgagcccaa atcctaagcc ggagccaaaa cctgaaccca
2581  aacctgagcc gagtcctaac cccaagccaa atcctaatcc caagccggag ccacagcctg
2641  atcctaagcc agaacccaag cctcagccag agccgtctca accaaagctg ccaccacttt
2701  caccagcaat agctataatt gtgcccggga actga
```

>3xABRC321i:OsRePRP2.1

(SEQ ID NO: 13)

```
   1  ggtaccgcaa cgcgtgtcct ccctacgtgg cggctcgaga ttgccaccgg ggtaccgcaa
  61  cgcgtgtcct ccctacgtgg cggctcgaga ttgccaccgg ggtaccgcaa cgcgtgtcct
 121  ccctacgtgg cggctcgaga ttgccaccgg tctagagtcg acctgcagca attccggcat
 181  gccgcagcac actataaata cctggccaga cacacaagct gaatgcatca gttctccatc
 241  gtactcttcg agagcacagc aagagagtga tcatttcagg taagatctag agtcgacctg
 301  caggcgaccg tatgtatatt accctatctc taccttgcaa atcgcgtgtg tacggatctt
 361  ctccgtggtc gagccgagtg attgctgatc tgatatccta tctgctgctt cgtttccttg
 421  cgcaggccaa gcatcacgct gctgtaccct ctgtaagttg atcagtcgct tgtggtactt
 481  tttagtacgt ggggaagtaa tccttgtgct ggatgtgacc ctggcggatc tgtataatac
 541  aggtatgcgg atcccccggg ctgcaggaat tcgatatcaa gctcaccatg aggagatcaa
 601  tcctctcact gtgcttccat ttggcgcttg tcattgcatt ggcagcaaat gttcctgaca
 661  ttgccaatgg acgcgtgatt gaagctaaat ctgatccaaa gccagcagat cccaagccta
 721  aacctgaccc aacaccaaaa ccacaaccag agacaaagcc cagtccacag cctaaccctc
 781  aacctaaccc acagccagat ccaaaaccat caccgcagcc tgatccaaaa cctacaccac
 841  agcctgaacc aaaacaagat cctcaaccaa acccacagcc ggatccaaaa caatcgccgc
 901  agcctgaccc aaaacctaca ccacagccta acccaaaaca agatcctcaa ccgaacccac
 961  aacctgaccc aaaaccaacg ctgcaaccta acccaaaaca agatcctcag ccgaacccac
1021  agcctaaccc gaaaccaacg ccacagcttg acccgaaaca agatcctcaa ccgaacccac
1081  aacctagccc caaagctgac ccaaaaccaa atccaaagcc taagccacaa ccggagccga
1141  gcccaaatcc taagccggag ccaaaacctg aacccaaacc tgagccgagt cctaaccccca
1201  agccaaatcc taatcccaag ccggagccac agcctgatcc taagccagaa cccaagcctc
1261  agccagagcc gtctcaacca aagctgccac cactttcacc agcaatagct ataattgtgc
1321  ccgggaactg a
```

```
>35S:OsRePRP2.1
                                                          (SEQ ID NO: 14)
   1    tcgagggatc cgtcccccgt gttctctcca aatgaaatga acttccttat atagaggaag
  61    ggtcttgcga aggatagtgg gattgtgcgt catcccttac gtcagtggag attccagata
 121    ggcctaacgc ttgtccaaga tctattcagg attccagata ggcctaacgc ttgtccaaga
 181    tctattcagg atatcacatc aatccacttg ctttgaagac gtggttggaa cgtcttcttt
 241    ttccacgatg ctcctcgtgg gtgggggtcc atctttggga ccactgtcgg cagaggcatc
 301    ttcaacgatg gccttt cctt tatcgcaatg atggcatttg taggagccac cttccttttc
 361    cactatcttc acaataaagt gacagatagc tgggcaatgg aatccgagga ggtttccgga
 421    taatgaggag atcaatcctc tcactgtgct tccatttggc gcttgtcatt gcattggcag
 481    caaatgttcc tgacattgcc aatggacgcg tgattgaagc taaatctgat ccaaagccag
 541    cagatcccaa gcctaaacct gacccaacac caaaaccaca accagagaca aagcccagtc
 601    cacagcctaa ccctcaacct aacccacagc cagatccaaa accatcaccg cagcctgatc
 661    caaaacctac accacagcct gaaccaaaac aagatcctca accaaaccca cagccggatc
 721    caaaacaatc gccgcagcct gacccaaaac ctacaccaca gcctaaccca aaacaagatc
 781    ctcaaccgaa cccacaacct gacccaaaac caacgctgca acctaaccca aaacaagatc
 841    ctcagccgaa cccacagcct aacccgaaac caacgccaca gcttgacccg aaacaagatc
 901    ctcaaccgaa cccacaacct agccccaaag ctgacccaaa accaaatcca aagcctaagc
 961    cacaaccgga gccgagccca atcctaagcc ggagccaaaa cctgaaccca aacctgagc
1021    cgagtcctaa ccccaagcca atcctaatcc caagccggag ccacagcct gatcctaagc
1081    cagaacccaa gcctcagcca gagccgtctc aaccaaagct gccaccactt tcaccagcaa
1141    tagctataat tgtgcccggg aactacccat acgatgttcc agattacgct tga
```

What is claimed is:

1. A method of improving stress tolerance while preventing growth reduction of a plant, comprising:
    (a) transforming plant cells with a vector comprising a nucleic acid operably linked to a promoter to obtain recombinant plant cells expressing a Repetitive Proline-rich Protein (RePRP), wherein the nucleic acid encodes the RePRP protein, wherein the vector comprises SEQ ID NO: 12, 13 or 14;
    (b) growing the recombinant plant cells obtained in (a) to generate a plurality of transgenic plants; and
    (c) selecting a transgenic plant from the plurality of transgenic plants generated in (b) that exhibits an improved tolerance to stress and substantially no growth reduction, as compared with a non-transgenic plant counterpart growing under the same conditions.

2. The method of claim 1, wherein the transgenic plant exhibits less yield reduction as compared with a non-transgenic plant counterpart.

3. The method of claim 1, wherein the transgenic plant is a monocot plant.

4. The method of claim 3, wherein the monocot plant is rice, barley, wheat, rye, oat, corn, bamboo, sugarcane, onion, leek or ginger.

5. The method of claim 1, wherein, the transgenic plant is a dicot plant.

6. The method of claim 5, wherein, the transgenic plant is *Arabidopsis*, soybean, peanut, sunflower, safflower, cotton, tobacco, tomato, pea, chickpea, pigeon pea or potato.

7. The method of claim 1, wherein the stress is abiotic stress selected from the group consisting of osmotic stress, drought stress, salt stress, or a combination thereof.

8. The method of claim 1, wherein the vector comprises SEQ ID NO: 12.

9. The method of claim 1, wherein the vector comprises SEQ ID NO: 13.

10. The method of claim 1, wherein the vector comprises SEQ ID NO: 14.

11. A method of improving stress tolerance while preventing reduction in growth and/or productivity of a plant, comprising:
(a) transforming plant cells with a vector comprising a nucleic acid operably linked to a promoter to obtain recombinant plant cells expressing a Repetitive Proline-rich Protein (RePRP), wherein the nucleic acid encodes the RePRP protein, wherein the vector comprises SEQ ID NO: 12, 13 or 14;
(b) growing the recombinant plant cells obtained in (a) to generate a plurality of transgenic plants; and
(c) selecting a transgenic plant from the plurality of transgenic plants generated in (b) that exhibits an improved tolerance to stress and substantially no reduction in growth and productivity, as compared with a non-transgenic plant counterpart growing under the same conditions.

12. The method of claim 11, wherein the vector comprises SEQ ID NO: 12.

13. The method of claim 11, wherein the vector comprises SEQ ID NO: 13.

14. The method of claim 1, wherein the RePRP protein is from rice, barley, wheat, maize and sorghum.

15. The method of claim 11, wherein the ReEPRP protein is from rice, barley, wheat, maize and sorghum.

16. The method of claim 11, wherein the vector comprises SEQ ID NO: 14.

* * * * *

SEQUENCE LISTING

<160> NUMBER OF SEQ ID NOS: 25

<210> SEQ ID NO 1
<211> LENGTH: 358
<212> TYPE: PRT
<213> ORGANISM: Oryza sativa

<400> SEQUENCE: 1

Met Ala Arg Arg Ser Pro Cys Leu Thr Ala Ala Val Leu Leu Leu Gly
1               5                   10                  15

Ala Leu Ala Val Ala Ser Ala Leu Val Asp Glu Ala Ala Ala Ala Gly
            20                  25                  30

Gln Gly Leu Gly His Gly Ala Arg Phe Met Ser Lys Gln Gly Arg Ala
        35                  40                  45

Met Tyr Glu Lys Pro Pro Glu Leu Glu Pro Lys Pro Lys Pro Lys Pro
    50                  55                  60

His Pro Lys His Glu Ser Lys Pro Glu Pro Lys Pro Glu Pro Lys Pro
65                  70                  75                  80

Glu Pro Lys Pro Tyr Pro Glu Pro Lys Pro Glu Thr Lys Pro Glu Leu
                85                  90                  95

Lys Pro Glu Pro Lys Pro Asn Pro Glu Pro Lys Pro Glu Pro Lys Pro
            100                 105                 110

Glu Pro Lys Pro Glu Pro Lys Pro Tyr Pro Glu Pro Lys Pro Lys Pro
        115                 120                 125

```
Lys Pro Glu Pro Lys Pro Glu Pro Lys Pro Glu His Lys Pro Glu Pro
        130                 135                 140

Lys Pro Glu Pro Glu Pro Lys Pro Tyr Pro Lys Pro Lys Pro Glu Pro
145                 150                 155                 160

Lys Pro Gly Pro Lys Pro Glu Pro Lys Pro Glu Pro Lys Pro His Pro
            165                 170                 175

Glu Pro Lys Pro Glu Pro Lys Pro Lys Pro Val Pro His Pro Glu Pro
            180                 185                 190

Lys Pro Glu Pro Lys Pro Glu Pro Lys Pro His Pro Glu Pro Lys Pro
        195                 200                 205

Glu Pro Lys Pro Glu Pro Lys Leu His Pro Lys Pro Glu Pro Lys Pro
        210                 215                 220

His Pro Glu Pro Glu Pro Lys Leu Lys Pro Glu Pro Lys Pro Glu Pro
225                 230                 235                 240

Lys Pro Glu Pro Glu Pro Lys Pro Glu Pro Lys Pro Glu Pro Lys Pro
            245                 250                 255

Glu Pro Lys Pro Tyr Pro Lys Pro Lys Pro Glu Pro Lys Pro Val Pro
            260                 265                 270

Lys Pro Lys Pro Ile Pro His Pro Gly Pro Lys Pro Lys Pro Lys Pro
        275                 280                 285

Asp Pro Lys Leu Glu Pro Lys Pro His Pro Glu Pro Lys Pro His Pro
        290                 295                 300

Met Pro Glu Pro Glu Pro Lys Pro Lys Pro Glu Pro Lys Pro Glu Pro
305                 310                 315                 320

Lys Pro Tyr Pro Glu Pro Lys Pro Lys Leu Lys Pro Glu Pro Lys Pro
            325                 330                 335

Gly Pro Lys Pro Ile Ala Pro Pro Asn Lys His Lys Pro Pro His Met
            340                 345                 350

Pro Pro Ala Thr Asn Gln
            355

<210> SEQ ID NO 2
<211> LENGTH: 416
<212> TYPE: PRT
<213> ORGANISM: Oryza sativa

<400> SEQUENCE: 2

Met Ala Arg Arg Ser Pro Cys Leu Ala Val Ala Met Leu Leu Leu Gly
1               5                   10                  15

Ala Leu Ala Val Ala Ser Ala Phe Ile Asp Glu Ala Ala Ala Ala Gly
            20                  25                  30

Arg Gly Leu Gly His Gly Ala Arg Phe Met Ser Lys Gln Gly Arg Val
        35                  40                  45

Thr Tyr Glu Lys Leu Pro Pro Glu Pro Lys Pro Lys Pro Lys Pro
    50                  55                  60

His Pro Lys Pro Thr Pro Lys Pro Glu Pro Lys Pro Glu Pro Glu Pro
65                  70                  75                  80

Lys Pro Val Pro Glu Pro Glu Pro Lys Pro Glu Pro Lys Pro Glu Pro
                85                  90                  95

Lys Pro Glu Pro Lys Pro Glu Pro Lys Pro Tyr Pro Glu Pro Lys Pro
            100                 105                 110

Glu Pro Lys Pro Glu Pro Lys Pro Glu Pro Lys Pro Glu Pro Lys Pro
        115                 120                 125

Lys Pro Glu Pro Lys Pro Glu Pro Lys Pro Tyr Pro Glu Pro Lys Pro
        130                 135                 140
```

```
Glu Pro Lys Pro Glu Pro Lys Pro Glu Pro Lys Pro Glu Pro Lys Pro
145                 150                 155                 160

Lys Pro Glu Pro Lys Pro His Pro Glu Pro Lys Pro Asp Pro Lys Pro
            165                 170                 175

Glu Pro Lys Pro His Pro Glu Pro Glu Pro Lys Pro Glu Pro Lys Pro
        180                 185                 190

Glu Pro Lys Pro His Pro Glu Pro Glu Pro Lys Pro Glu Pro Lys Pro
        195                 200                 205

Glu Pro Lys Pro Glu Pro Lys Pro Glu Pro Lys Pro Glu Pro Lys Pro
    210                 215                 220

Lys Pro Lys Pro Glu Pro Lys Pro Lys Pro Glu Pro Lys Pro Tyr Pro
225                 230                 235                 240

Glu Pro Lys Pro Lys Pro Glu Pro Lys Pro Glu Pro Lys Pro Glu Pro
            245                 250                 255

Lys Pro Glu Pro Lys Pro Glu Pro Lys Pro Glu Pro Lys Pro Glu Pro
        260                 265                 270

Lys Pro Glu Pro Lys Pro Lys Pro Glu Pro Lys Pro His Pro Lys Pro
    275                 280                 285

Glu Pro Lys Pro Glu Pro Lys Pro Glu Pro Lys Pro Glu Pro Lys Pro
290                 295                 300

Glu Pro Lys Pro Glu Pro Lys Pro Glu Pro Glu Pro Lys Pro Glu Pro
305                 310                 315                 320

Lys Pro Glu Pro Lys Pro Glu Pro Lys Pro Tyr Pro Glu Pro Lys Pro
            325                 330                 335

Asp Pro Lys Pro Glu Pro Lys Pro His Pro Glu Pro Lys Pro Glu Pro
        340                 345                 350

Lys Pro Gln Pro Glu Pro Lys Pro Glu Pro Lys Pro Glu Pro Lys Pro
        355                 360                 365

Glu Pro Lys Pro Glu Pro Lys Pro Glu Pro Lys Pro Tyr Pro Glu Pro
    370                 375                 380

Lys Pro Glu Pro Lys Pro Lys Pro Lys Pro Glu Pro Lys Pro Glu Ala
385                 390                 395                 400

Pro Pro Lys Lys His Lys Pro Pro His Ile Pro Pro Ala Thr Asp Gln
            405                 410                 415

<210> SEQ ID NO 3
<211> LENGTH: 247
<212> TYPE: PRT
<213> ORGANISM: Oryza sativa

<400> SEQUENCE: 3

Met Arg Ser Ile Leu Ser Leu Cys Phe His Leu Ala Leu Ala Ile Ala
1               5                   10                  15

Leu Ala Ala Asn Val Pro Asp His Ile Ala Asn Gly Arg Val Ile Glu
            20                  25                  30

Ala Lys Ser Asp Pro Lys Pro Ala Asp Pro Asn Pro Lys Pro Asp Pro
        35                  40                  45

Thr Pro Lys Pro Gln Pro Glu Thr Lys Pro Ser Pro Gln Pro Asn Pro
    50                  55                  60

Gln Pro Asn Pro Gln Pro Asp Pro Lys Pro Ser Pro Gln Pro Asp Pro
65                  70                  75                  80

Lys Pro Thr Pro Gln Pro Glu Pro Lys Gln Asp Pro Lys Pro Asn Pro
            85                  90                  95

Gln Pro Asp Pro Lys Pro Ser Pro Gln Pro Asp Pro Lys Pro Thr Pro
```

```
                100             105                 110
Gln Pro Asp Pro Lys Gln Asp Pro Gln Pro Asn Pro Gln Pro Asp Pro
            115                 120                 125
Lys Pro Thr Pro Gln Pro Asn Pro Lys Gln Asp Pro Gln Pro Asn Pro
130                 135                 140
Gln Pro Asp Pro Lys Pro Thr Pro Gln Pro Asp Pro Lys Gln Asp Pro
145                 150                 155                 160
Gln Pro Asn Pro Gln Pro Ser Pro Lys Ala Asp Pro Lys Pro Asn Pro
                165                 170                 175
Lys Pro Lys Pro Gln Pro Glu Pro Ser Pro Asn Pro Lys Pro Glu Pro
            180                 185                 190
Lys Pro Glu Pro Lys Pro Glu Pro Ser Pro Asn Pro Lys Pro Asn Pro
            195                 200                 205
Asn Pro Lys Pro Glu Pro Gln Pro Asp Pro Lys Pro Glu Pro Lys Pro
            210                 215                 220
Gln Pro Glu Pro Ser Leu Pro Lys Pro Pro Leu Ser Pro Ala Ile
225                 230                 235                 240
Ala Ile Ile Val Pro Gly Asn
                245

<210> SEQ ID NO 4
<211> LENGTH: 247
<212> TYPE: PRT
<213> ORGANISM: Oryza sativa

<400> SEQUENCE: 4

Met Arg Arg Ser Ile Leu Ser Leu Cys Phe His Leu Ala Leu Val Ile
1               5                   10                  15
Ala Leu Ala Ala Asn Val Pro Asp Ile Ala Asn Gly Arg Val Ile Glu
            20                  25                  30
Ala Lys Ser Asp Pro Lys Pro Ala Asp Pro Lys Pro Lys Pro Asp Pro
        35                  40                  45
Thr Pro Lys Pro Gln Pro Glu Thr Lys Pro Ser Pro Gln Pro Asn Pro
    50                  55                  60
Gln Pro Asn Pro Gln Pro Asp Pro Lys Pro Ser Pro Gln Pro Asp Pro
65                  70                  75                  80
Lys Pro Thr Pro Gln Pro Glu Pro Lys Gln Asp Pro Gln Pro Asn Pro
                85                  90                  95
Gln Pro Asp Pro Lys Gln Ser Pro Gln Pro Asp Pro Lys Pro Thr Pro
            100                 105                 110
Gln Pro Asn Pro Lys Gln Asp Pro Gln Pro Asn Pro Gln Pro Asp Pro
            115                 120                 125
Lys Pro Thr Leu Gln Pro Asn Pro Lys Gln Asp Pro Gln Pro Asn Pro
        130                 135                 140
Gln Pro Asn Pro Lys Pro Thr Pro Gln Leu Asp Pro Lys Gln Asp Pro
145                 150                 155                 160
Gln Pro Asn Pro Gln Pro Ser Pro Lys Ala Asp Pro Lys Pro Asn Pro
                165                 170                 175
Lys Pro Lys Pro Gln Pro Glu Pro Ser Pro Asn Pro Lys Pro Glu Pro
            180                 185                 190
Lys Pro Glu Pro Lys Pro Glu Pro Ser Pro Asn Pro Lys Pro Asn Pro
            195                 200                 205
Asn Pro Lys Pro Glu Pro Gln Pro Asp Pro Lys Pro Glu Pro Lys Pro
            210                 215                 220
```

Gln Pro Glu Pro Ser Gln Pro Lys Leu Pro Pro Leu Ser Pro Ala Ile
225                 230                 235                 240

Ala Ile Ile Val Pro Gly Asn
            245

<210> SEQ ID NO 5
<211> LENGTH: 1493
<212> TYPE: DNA
<213> ORGANISM: Oryza sativa

<400> SEQUENCE: 5

| | | | | | |
|---|---|---|---|---|---|
| caacagcaga | agtgagagag | ggagaagaag | ataagcgaag | aggaggagct | tagcttgcca | 60 |
| gccatggcta | ggcgctctcc | ttgcctcact | gccgccgtgc | tcctgcttgg | ggcattggcg | 120 |
| gtggcgagcg | ctttagttga | tgaagcggcg | gcagctggcc | agggactcgg | ccatggcgcc | 180 |
| cgcttcatga | gcaagcaggg | ccgtgcgatg | tacgagaagc | cgccagagct | ggagccgaag | 240 |
| ccaaagccaa | agcctcatcc | taagcatgaa | tcaaaaccgg | agccaaagcc | agaacctaag | 300 |
| ccggagccaa | agccataccc | agagccgaag | ccagagacga | accggagct | aaagccagaa | 360 |
| ccaaaaccta | tccagaacc | taaacctgag | cctaagcctg | aaccaaaacc | agaaccaaag | 420 |
| ccatacccag | agccgaagcc | aaagcccaaa | ccggagccaa | agcagaaccc | aaaacctgag | 480 |
| cataaacctg | aaccaaaacc | agaaccagaa | ccaaagccat | acccaaagcc | aaagccagag | 540 |
| ccaaaaccgg | ggcccaaacc | cgagccgaag | ccagagccta | agcacacccc | agaaccgaaa | 600 |
| ccggagccca | aaccaaagcc | agtgccacac | cctgaaccaa | aaccggaacc | aaagccggag | 660 |
| cccaaaccac | acccagaacc | aaagcctgag | ccgaaaccg | agcctaagct | acacccgaag | 720 |
| cctgagccaa | agccacaccc | agagcctgag | cctaagctta | aacctgaacc | aaaaccagag | 780 |
| ccaaagccag | agcctgaacc | gaagcccgag | ccaaagcctg | aaccaaaacc | agagcctaaa | 840 |
| ccatatccaa | agccaaaacc | ggaacctaaa | ccggtgccga | agccgaagcc | cattccacac | 900 |
| ccaggaccaa | aaccaaagcc | taaacctgac | ccaaagctag | agcccaagcc | acacccggag | 960 |
| ccaaaaccac | atccgatgcc | tgaacctgaa | ccaaagccta | agcccgaacc | aaagccagag | 1020 |
| cctaaaccat | acccagaacc | aaagcctaaa | ctgaaacctg | aacctaagcc | tggaccgaaa | 1080 |
| cctatagcac | cgccgaacaa | gcacaagccg | ccgcacatgc | caccagcgac | aaaccagtga | 1140 |
| cggcgatcgc | tggagaccga | gcatttgctg | gctgcacggt | tgaggcaccg | acgacattat | 1200 |
| ttcacccgag | gaaggagcgc | tagcgagtca | ctacactgta | ccgtttctgg | aataaagtga | 1260 |
| tgagctagct | ttctgcttgc | cttttctttt | cctctcttat | tttcctttta | tttcatgttg | 1320 |
| gttttttcgga | tgtgccactg | ctagctagtg | taattaaatt | atttattatg | tgcctaccgt | 1380 |
| catttttatt | accgtgtctg | tgacattcta | ttgtctattg | gcattattct | cattgtaaaa | 1440 |
| tcttttggta | atattatttg | tcatcatttt | tacccagctt | ctaaaaaaaa | aaa | 1493 |

<210> SEQ ID NO 6
<211> LENGTH: 1251
<212> TYPE: DNA
<213> ORGANISM: Oryza sativa

<400> SEQUENCE: 6

| | | | | | |
|---|---|---|---|---|---|
| atggcgaggc | gctctccttg | cctcgccgtc | gccatgctcc | tgcttggggc | gttggcggtg | 60 |
| gcgagcgcct | tcattgatga | agcggcggct | gctggccggg | ggctcggcca | tggcgcccgc | 120 |
| ttcatgagca | agcagggtcg | tgtgacatac | gagaagctgc | cggagccgga | gccgaagcca | 180 |
| aagccaaagc | ctcatcctaa | acccacgcca | aaacctgagc | ccaagccaga | gccggagcca | 240 |

```
aaaccagtac ctgagcctga gcctaaaccg gaaccaaagc cagaaccaaa acctgagcct      300
aagcctgaac ctaaaccata cccagagcca aaaccggagc cgaagccaga gccaaaacct      360
gagccggagc ctaaacctga gcctaagcca gaaccaaaac cagaaccaaa gccgtaccca      420
gagccgaagc cagagccaaa accggaaccg aagccggaac caaaaccgga gcccaaacca      480
aagccagagc ccaaaccaca cccagaacca agcctgatcc gaaacctgag cctaagcca       540 cacccagagc ctgagcctaa gcctgaacct aagcctgagc caagccaca ccctgagcct       600 gaaccaaagc ctgagcctaa gctgagcca agccagaac caaagccgga gccaaaacct        660
gaaccaaaac caaagccaaa gccagagcca agccaaagc ctgagcccaa gccatacct        720 gagcctaagc ctaagcctga ccaaagcct gagcctaagc ctgagccaaa gccagaacca       780
aagccggagc caaaacctga ccaaaacca gagccaaagc cagagccaaa gccaaagcct       840
gagcccaagc cacacccctaa gcctgagcct aagcctgagc ccaagccaga accaaagcca     900
gagccaaaac ctgaaccaaa accagagcca aaaccagagc ctgaaccgaa gcctgagcca      960
aagcctgaac caaaaccaga gcccaaacca tatccagagc ctaaaccgga tcccaaacca     1020
gaacccaaac cacacccaga accaaagcca gagcccaagc cacagccgga gccaaaacca     1080
gagccgaagc ctgaacctaa accagagcct aagcccgaac caaaaccgga gcctaaacca     1140
tacccagagc caaagcctga accgaaacct aagcctaagc ctgagccaaa acctgaagca     1200
cctccgaaga agcacaagcc gccgcacata ccgccagcga ccgaccagtg a             1251

<210> SEQ ID NO 7
<211> LENGTH: 1088
<212> TYPE: DNA
<213> ORGANISM: Oryza sativa

<400> SEQUENCE: 7
aacacaccta actaccacag cttgtgaact atcaagagtg agtagtagag tttgcagtga       60
caacgagatg aggagatcaa tcctctcact gtgcttccat ttggcgcttg tcattgcatt      120
ggcagcaaat gttcctgaca ttgccaatgg acgcgtgatt gaagctaaat ctgatccaaa      180
gccagcagat cccaagccta aacctgaccc aacaccaaaa ccacaaccag agacaaagcc      240
cagtccacag cctaaccctc aacctaaccc acagccagat ccaaaaccat caccgcagcc      300
tgatccaaaa cctacaccac agcctgaacc aaaacaagat cctcaaccaa acccacagcc      360
ggatccaaaa caatcgccgc agcctgaccc aaaacctaca ccacagccta acccaaaaca      420
agatcctcaa ccgaacccac aacctgaccc aaaaccaacg ctgcaaccta cccaaaaaca      480
agatcctcag ccgaacccac agcctaaccc gaaaccaacg ccacagcttg acccgaaaca      540
agatcctcaa ccgaacccac aacctagccc caaagctgac ccaaaaccaa atccaaagcc      600
taagccacaa ccggagccga gcccaaatcc taagccggag ccaaaacctg aacccaaacc      660
tgagccgagt cctaaccccca agccaaatcc taatccaag ccggagccac agcctgatcc      720
taagccagaa cccaagcctc agccagagcc gtctcaacca aagctgccac cactttcacc      780
agcaatagct ataattgtgc ccgggaactg agtagacttg gttgtttgct acgtatgatc      840
ccgcatactt ttggtatgta ctattgctct agtgactatt tgtgtgtttt tcgtgtgttg      900
ttcactagtg tgtccatgtg gctatctatg tgttttctta atgccgttgc atatgagcag      960
gcgtgcttct tataataaag catacataca tacatacata catacataca tacatatata     1020
tatacacgtg tgttatgtat gtgcgtacat accatcaata aaagagcat gtatccctgt     1080
```

```
gtgtcaat                                                                   1088
```

<210> SEQ ID NO 8
<211> LENGTH: 1057
<212> TYPE: DNA
<213> ORGANISM: Oryza sativa

<400> SEQUENCE: 8

```
aacacaccta gctaccacag cttgtgtact gtcaagagtg agtagtagag tttgtagtga     60
caacgagatg agatcaatcc tctcactgtg cttccatttg gcgcttgcca ttgcattggc    120
ggcaaatgtt cctgatcaca ttgccaatgg acgcgtgatt gaagctaaat ctgatccaaa    180
gccagcagat cccaatccta aacctgaccc aacaccaaaa ccacaaccag agacaaagcc    240
cagtccacag cctaaccctc aacctaaccc acagccagat ccaaaaccat caccgcagcc    300
tgacccaaaa cctacaccac agcctgaacc aaaacaagat cctaaaccaa acccacaacc    360
ggatccaaaa ccatctccgc agcctgaccc gaaacctaca cccacagcctg acccaaaaca    420
agatcctcaa ccgaacccac aacctgaccc aaaaccaacg ccgcaaccta cccaaaaca    480
agatcctcag ccgaacccac agcctgaccc aaaaccaacg ccacagcctg acccgaaaca    540
agatcctcaa ccgaacccgc aacctagccc caaagctgac ccaaaaccaa atccaaagcc    600
taagccacaa ccggagccga cccaaatcc taagccggag ccaaagcctg aacccaaacc    660
tgagccaagt cctaacccca agccaaatcc taatcctaag ccggagccac agcctgatcc    720
taagccagaa cccaagcctc agccagagcc atctctgcca aagccaccac ctctttcacc    780
agcaatagct ataattgtgc ccgggaactg agtagactt ttgctacgta tgattccgca    840
tagttttggt atgtactatt gctctagtga ctatctatgt gtttgtcgtg tgttgttcac    900
tggtgtatgt gtccatgtgg ctatctatgt gttttcttaa tgctgttgca tctgagcagg    960
cgtgcttctt ataataaagc atatatatgc acgtgtgtta tgtatgtgcg tacatatata   1020
ccatgaataa aaagagcatg tatccctgtg tgtcact                             1057
```

<210> SEQ ID NO 9
<211> LENGTH: 166
<212> TYPE: DNA
<213> ORGANISM: Artificial Sequence
<220> FEATURE:
<223> OTHER INFORMATION: Synthetic promoter: 1XABRC321

<400> SEQUENCE: 9

```
ggtaccgcaa cgcgtgtcct ccctacgtgg cggctcgaga ttgccaccgg tctagagtcg     60
actgcagcaa ttccggcatg ccgcagcaca ctataaatac ctggccagac acacaagctg    120
aatgcatcag ttctccatcg tactcttcga gagcacagca agagag                   166
```

<210> SEQ ID NO 10
<211> LENGTH: 216
<212> TYPE: DNA
<213> ORGANISM: Artificial Sequence
<220> FEATURE:
<223> OTHER INFORMATION: Synthetic promoter: 2XABRC321

<400> SEQUENCE: 10

```
ggtaccgcaa cgcgtgtcct ccctacgtgg cggctcgaga ttgccaccgg ggtaccgcaa     60
cgcgtgtcct ccctacgtgg cggctcgaga ttgccaccgg tctagagtcg actgcagcaa    120
ttccggcatg ccgcagcaca ctataaatac ctggccagac acacaagctg aatgcatcag    180
ttctccatcg tactcttcga gagcacagca agagag                              216
```

<210> SEQ ID NO 11
<211> LENGTH: 266
<212> TYPE: DNA
<213> ORGANISM: Artificial Sequence
<220> FEATURE:
<223> OTHER INFORMATION: Synthetic promoter: 3XABRC321

<400> SEQUENCE: 11

```
ggtaccgcaa cgcgtgtcct ccctacgtgg cggctcgaga ttgccaccgg ggtaccgcaa    60
cgcgtgtcct ccctacgtgg cggctcgaga ttgccaccgg ggtaccgcaa cgcgtgtcct   120
ccctacgtgg cggctcgaga ttgccaccgg tctagagtcg actgcagcaa ttccggcatg   180
ccgcagcaca ctataaatac ctggccagac acacaagctg aatgcatcag ttctccatcg   240
tactcttcga gagcacagca agagag                                       266
```

<210> SEQ ID NO 12
<211> LENGTH: 2735
<212> TYPE: DNA
<213> ORGANISM: Artificial Sequence
<220> FEATURE:
<223> OTHER INFORMATION: Synthetic fused promoter/coding region:
      Ubi:OsRePRP2.1

<400> SEQUENCE: 12

```
ctgcagtgca gcgtgacccg gtcgtgcccc tctctagaga taatgagcat tgcatgtcta    60
agttataaaa aattaccaca tatttttttt gtcacacttg tttgaagtgc agtttatcta   120
tctttataca tatatttaaa ctttactcta cgaataatat aatctatagt actacaataa   180
tatcagtgtt ttagagaatc atataaatga acagttagac atggtctaaa ggacaattga   240
gtattttgac aacaggactc tacagtttta tcttttttagt gtgcatgtgt tctccttttt   300 tttttttgcaa atagcttcac ctatataata cttcatccat tttattagta catccattta   360
gggtttaggg ttaatggttt ttatagacta attttttttag tacatctatt ttattctatt   420
ttagcctcta aattaagaaa actaaaactc tattttagtt tttttatttta ataatttaga   480 tataaaatag aataaaataa agtgactaaa aattaaacaa ataccctttta agaaattaaa   540 aaaactaagg aaacatttttt cttgtttcga gtagataatg ccagcctgtt aaacgccgtc   600
gacgcagtct aacggacacc aaccagcgaa ccagcagcgt cgcgtcgggc caagcgaagc   660
agacggcacg gcatctctgt cgctgcctct ggaccccctct cgagagttcc gctccaccgt   720
tggacttcgt ccgctgtcgg catccagaaa ttgcgtggcg gagcggcaga cgtgagccgg   780
cacggcaggc ggcctcctcc tcctctcacg gcaccggcag ctacggggga ttccttttccc   840 accgctcctt cgctttccct tcctcgcccg ccgtaataaa tagacacccc ctccacaccc   900
tctttcccca acctcgtgtt gttcggagcg cacacacaca caaccagatc tccccccaaat   960 ccacccgtcg gcacctccgc ttcaaggtac gccgctcgtc ctccccccccc ctctctacct  1020 tctctagatc ggcgttccgg tccatggtta gggcccggta gttctacttc tgttcatgtt  1080
tgtgttagat ccgtgtttgt gttagatccg tgctgctagc gttcgtacac ggatgcgacc  1140
tgtacgtcag acacgttctg attgctaact tgccagtgtt tctctttggg gaatcctggg  1200
atggctctag ccgttccgca gacgggatcg atttcatgat ttttttttgtt tcgttgcata  1260 gggtttggtt tgcccttttc ctttatttca atatatgccg tgcacttgtt tgtcgggtca  1320
tcttttcatg ctttttttttg tcttggttgt gatgatgtgg tctggttggg cggtcgttct  1380
agatcggagt agaattctgt ttcaaactac ctggtggatt tattaatttt ggatctgtat  1440
```

```
gtgtgtgcca tacatattca tagttacgaa ttgaagatga tggatggaaa tatcgatcta    1500
ggataggtat acatgttgat gcgggtttta ctgatgcata tacagagatg cttttgttcg    1560
cttggttgtg atgatgtggt gtggttgggc ggtcgttcat tcgttctaga tcggagtaga    1620
atactgtttc aaactacctg gtgtatttat taatttggga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920 tacgctattt atttgcttgg tactgtttct tttgtcgatg ctcaccctgt gtttggtgt     1980 tacttctgca gatgaggaga tcaatcctct cactgtgctt ccatttggcg cttgtcattg    2040
cattggcagc aaatgttcct gacattgcca atggacgcgt gattgaagct aaatctgatc    2100
caaagccagc agatcccaag cctaaacctg acccaacacc aaaaccacaa ccagagacaa    2160
agcccagtcc acagcctaac cctcaaccta acccacagcc agatccaaaa ccatcaccgc    2220
agcctgatcc aaaacctaca ccacagcctg aaccaaaaca agatcctcaa ccaaacccac    2280
agccggatcc aaaacaatcg ccgcagcctg acccaaaacc tacaccacag cctaacccaa    2340
aacaagatcc tcaaccgaac ccacaacctg acccaaaacc aacgctgcaa cctaacccaa    2400
aacaagatcc tcagccgaac ccacagccta acccgaaacc aacgccacag cttgacccga    2460
aacaagatcc tcaaccgaac ccacaaccta gccccaaagc tgacccaaaa ccaaatccaa    2520
agcctaagcc acaaccggag ccgagcccaa atcctaagcc ggagccaaaa cctgaaccca    2580
aacctgagcc gagtcctaac cccaagccaa atcctaatcc caagccggag ccacagcctg    2640
atcctaagcc agaacccaag cctcagccag agccgtctca accaaagctg ccaccacttt    2700
caccagcaat agctataatt gtgcccggga actga                              2735
```

<210> SEQ ID NO 13
<211> LENGTH: 1331
<212> TYPE: DNA
<213> ORGANISM: Artificial Sequence
<220> FEATURE:
<223> OTHER INFORMATION: Synthetic fused promoter/coding region: 3xABRC321:OsRePRP2.1

<400> SEQUENCE: 13

```
ggtaccgcaa cgcgtgtcct ccctacgtgg cggctcgaga ttgccaccgg ggtaccgcaa      60
cgcgtgtcct ccctacgtgg cggctcgaga ttgccaccgg ggtaccgcaa cgcgtgtcct    120
ccctacgtgg cggctcgaga ttgccaccgg tctagagtcg acctgcagca attccggcat    180
gccgcagcac actataaata cctggccaga cacacaagct gaatgcatca gttctccatc    240
gtactcttcg agagcacagc aagagagtga tcatttcagg taagatctag agtcgacctg    300
caggcgaccg tatgtatatt accctatctc taccttgcaa atcgcgtgtg tacgatctt     360 ctccgtggtc gagccgagtg attgctgatc tgatatccta tctgctgctt cgtttccttg    420
cgcaggccaa gcatcacgct gctgtaccct ctgtaagttg atcagtcgct tgtggtactt    480
tttagtacgt ggggaagtaa tccttgtgct ggatgtgacc ctggcggatc tgtataatac    540
aggtatgcgg atcccccggg ctgcaggaat tcgatatcaa gctcaccatg aggagatcaa    600
tcctctcact gtgcttccat ttggcgcttg tcattgcatt ggcagcaaat gttcctgaca    660
ttgccaatgg acgcgtgatt gaagctaaat ctgatccaaa gccagcagat cccaagccta    720
```

| aacctgaccc aacaccaaaa ccacaaccag agacaaagcc cagtccacag cctaaccctc | 780 |
| aacctaaccc acagccagat ccaaaaccat caccgcagcc tgatccaaaa cctacaccac | 840 |
| agcctgaacc aaaacaagat cctcaaccaa acccacagcc ggatccaaaa caatcgccgc | 900 |
| agcctgaccc aaaacctaca ccacagccta acccaaaaca agatcctcaa ccgaacccac | 960 |
| aacctgaccc aaaaccaacg ctgcaaccta acccaaaaca agatcctcag ccgaacccac | 1020 |
| agcctaaccc gaaaccaacg ccacagcttg acccgaaaca agatcctcaa ccgaacccac | 1080 |
| aacctagccc caaagctgac ccaaaaccaa atccaaagcc taagccacaa ccggagccga | 1140 |
| gcccaaatcc taagccggag ccaaaacctg aacccaaacc tgagccgagt cctaacccca | 1200 |
| agccaaatcc taatcccaag ccggagccac agcctgatcc taagccagaa cccaagcctc | 1260 |
| agccagagcc gtctcaacca aagctgccac cactttcacc agcaatagct ataattgtgc | 1320 |
| ccgggaactg a | 1331 |

<210> SEQ ID NO 14
<211> LENGTH: 1193
<212> TYPE: DNA
<213> ORGANISM: Artificial Sequence
<220> FEATURE:
<223> OTHER INFORMATION: Synthetic fused promoter/coding region: 35S:OsRePRP2.1

<400> SEQUENCE: 14

| tcgagggatc cgtcccccgt gttctctcca aatgaaatga acttccttat atagaggaag | 60 |
| ggtcttgcga aggatagtgg gattgtgcgt catcccttac gtcagtggag attccagata | 120 |
| ggcctaacgc ttgtccaaga tctattcagg attccagata ggcctaacgc ttgtccaaga | 180 |
| tctattcagg atatcacatc aatccacttg ctttgaagac gtggttggaa cgtcttcttt | 240 |
| ttccacgatg ctcctcgtgg gtgggggtcc atctttggga ccactgtcgg cagaggcatc | 300 |
| ttcaacgatg gccttttcctt tatcgcaatg atggcatttg taggagccac cttccttttc | 360 |
| cactatcttc acaataaagt gacagatagc tgggcaatgg aatccgagga ggtttccgga | 420 |
| taatgaggag atcaatcctc tcactgtgct tccatttggc gcttgtcatt gcattggcag | 480 |
| caaatgttcc tgacattgcc aatggacgcg tgattgaagc taaatctgat ccaaagccag | 540 |
| cagatcccaa gcctaaacct gacccaacac caaaaccaca accagagaca agcccagtc | 600 |
| cacagcctaa ccctcaacct aacccacagc cagatccaaa accatcaccg cagcctgatc | 660 |
| caaaacctac accacagcct gaaccaaaac aagatcctca accaaaccca cagccggatc | 720 |
| caaaacaatc gccgcagcct gacccaaaac ctacaccaca gcctaaccca aaacaagatc | 780 |
| ctcaaccgaa cccacaacct gacccaaaac caacgctgca acctaaccca aaacaagatc | 840 |
| ctcagccgaa cccacagcct aacccgaaac caacgccaca gcttgacccg aaacaagatc | 900 |
| ctcaaccgaa cccacaacct agccccaaag ctgacccaaa accaaatcca aagcctaagc | 960 |
| cacaaccgga gccgagccca atcctaagc cggagccaaa acctgaaccc aaacctgagc | 1020 |
| cgagtcctaa ccccaagcca aatcctaatc ccaagccgga gccacagcct gatcctaagc | 1080 |
| cagaacccaa gcctcagcca gagccgtctc aaccaaagct gccaccactt tcaccagcaa | 1140 |
| tagctataat tgtgcccggg aactacccat acgatgttcc agattacgct tga | 1193 |

<210> SEQ ID NO 15
<211> LENGTH: 28
<212> TYPE: DNA
<213> ORGANISM: Artificial Sequence

```
<220> FEATURE:
<223> OTHER INFORMATION: Synthetic: OsRePRP1.1 primer F

<400> SEQUENCE: 15
acaagctcac agttcagtta cgtacaac                                          28

<210> SEQ ID NO 16
<211> LENGTH: 17
<212> TYPE: DNA
<213> ORGANISM: Artificial Sequence
<220> FEATURE:
<223> OTHER INFORMATION: Synthetic: OsRePRP1.1 primer R

<400> SEQUENCE: 16
gcgctccttc ctcgggt                                                      17

<210> SEQ ID NO 17
<211> LENGTH: 25
<212> TYPE: DNA
<213> ORGANISM: Artificial Sequence
<220> FEATURE:
<223> OTHER INFORMATION: Synthetic: OsRePRP1.2 primer F

<400> SEQUENCE: 17
gatcacagaa gctcacagtt cagtt                                             25

<210> SEQ ID NO 18
<211> LENGTH: 18
<212> TYPE: DNA
<213> ORGANISM: Artificial Sequence
<220> FEATURE:
<223> OTHER INFORMATION: Synthetic: OsRePRP1.2 primer R

<400> SEQUENCE: 18
tgactcgctc gctcctcc                                                     18

<210> SEQ ID NO 19
<211> LENGTH: 24
<212> TYPE: DNA
<213> ORGANISM: Artificial Sequence
<220> FEATURE:
<223> OTHER INFORMATION: Synthetic: OsRePRP2.1 primer F

<400> SEQUENCE: 19
atgaggagat caatcctctc actg                                              24

<210> SEQ ID NO 20
<211> LENGTH: 23
<212> TYPE: DNA
<213> ORGANISM: Artificial Sequence
<220> FEATURE:
<223> OTHER INFORMATION: Synthetic: OsRePRP2.1 primer R

<400> SEQUENCE: 20
tcagttcccg ggcacaatta tag                                               23

<210> SEQ ID NO 21
<211> LENGTH: 24
<212> TYPE: DNA
<213> ORGANISM: Artificial Sequence
<220> FEATURE:
<223> OTHER INFORMATION: Synthetic: OsRePRP2.2 primer F

<400> SEQUENCE: 21
aatgttcctg atcacattgc caat                                              24
```

```
<210> SEQ ID NO 22
<211> LENGTH: 24
<212> TYPE: DNA
<213> ORGANISM: Artificial Sequence
<220> FEATURE:
<223> OTHER INFORMATION: Synthetic: OsRePRP2.2 primer R

<400> SEQUENCE: 22
cataccaaaa ctatgcggaa tcat                                           24

<210> SEQ ID NO 23
<211> LENGTH: 20
<212> TYPE: DNA
<213> ORGANISM: Artificial Sequence
<220> FEATURE:
<223> OTHER INFORMATION: Synthetic: OsActin primer F

<400> SEQUENCE: 23
ctgatggaca ggttatcacc                                                20

<210> SEQ ID NO 24
<211> LENGTH: 22
<212> TYPE: DNA
<213> ORGANISM: Artificial Sequence
<220> FEATURE:
<223> OTHER INFORMATION: Synthetic: OsActin primer R

<400> SEQUENCE: 24
caggtagcaa taggtattac ag                                             22

<210> SEQ ID NO 25
<211> LENGTH: 4
<212> TYPE: PRT
<213> ORGANISM: Artificial Sequence
<220> FEATURE:
<223> OTHER INFORMATION: Synthetic: proline-rich motif
<220> FEATURE:
<221> NAME/KEY: misc_feature
<222> LOCATION: (2)..(2)
<223> OTHER INFORMATION: Xaa can be any naturally occurring amino acid
      except proline
<220> FEATURE:
<221> NAME/KEY: misc_feature
<222> LOCATION: (4)..(4)
<223> OTHER INFORMATION: Xaa can be any naturally occurring amino acid
      except proline

<400> SEQUENCE: 25

Pro Xaa Pro Xaa
1
```